(12) United States Patent
Kim et al.

(10) Patent No.: US 11,273,188 B2
(45) Date of Patent: Mar. 15, 2022

(54) STRAIN HAVING ABILITY TO INHIBIT OBESITY AND PHARMACEUTICAL COMPOSITION CONTAINING SAME

(71) Applicant: MICROBIOTICA GMBH, Inning Am Ammersee (DE)

(72) Inventors: Hyeon Jin Kim, Wanju gun (KR); Seong Tshool Hong, Jeonju-si (KR); Jae Gak Yu, Seocheon-gun (KR)

(73) Assignee: MICROBIOTICA GMBH, Inning am Ammersee (DE)

( * ) Notice: Subject to any disclaimer, the term of this patent is extended or adjusted under 35 U.S.C. 154(b) by 393 days.

(21) Appl. No.: 15/774,328

(22) PCT Filed: Nov. 8, 2016

(86) PCT No.: PCT/KR2016/012791
§ 371 (c)(1),
(2) Date: May 8, 2018

(87) PCT Pub. No.: WO2017/082611
PCT Pub. Date: May 18, 2017

(65) Prior Publication Data
US 2020/0061132 A1   Feb. 27, 2020

(30) Foreign Application Priority Data
Nov. 9, 2015  (KR) .................. 10-2015-0156733

(51) Int. Cl.
| | |
|---|---|
| *A61K 35/744* | (2015.01) |
| *A61K 35/747* | (2015.01) |
| *A61K 35/74* | (2015.01) |
| *A23L 33/10* | (2016.01) |
| *A23L 33/135* | (2016.01) |
| *C12R 1/225* | (2006.01) |
| *C12N 1/20* | (2006.01) |
| *A61P 3/04* | (2006.01) |
| *A61K 9/00* | (2006.01) |
| *A61K 35/00* | (2006.01) |

(52) U.S. Cl.
CPC .......... *A61K 35/744* (2013.01); *A23L 33/135* (2016.08); *A61K 9/0056* (2013.01); *A61K 35/747* (2013.01); *A61P 3/04* (2018.01); *A23V 2002/00* (2013.01); *A23Y 2220/71* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 7,001,756 | B1 | 2/2006 | Hsu et al. |
| 8,257,695 | B2 | 9/2012 | Rautonen et al. |
| 8,318,150 | B2 | 11/2012 | Arigoni et al. |
| 8,318,151 | B2 | 11/2012 | Darimont-Nicolau et al. |
| 8,440,178 | B2 | 5/2013 | Darimont et al. |
| 8,440,179 | B2 | 5/2013 | Kawakami et al. |
| 8,454,949 | B2 | 6/2013 | Arigoni et al. |
| 8,637,000 | B2 | 1/2014 | Morita et al. |
| 2008/0057044 | A1 | 3/2008 | Lee et al. |
| 2008/0267932 | A1* | 10/2008 | Lee ...................... A61K 35/747 424/93.45 |
| 2009/0181437 | A1 | 7/2009 | Kudo et al. |
| 2010/0254956 | A1* | 10/2010 | Arulampalam ...... A61K 35/745 424/93.45 |

FOREIGN PATENT DOCUMENTS

| | | |
|---|---|---|
| EP | 2 123 168 B1 | 12/2011 |
| KR | 10-2004-0027180 A | 4/2004 |
| KR | 10-0543114 B1 | 1/2006 |
| KR | 10-0794701 B1 | 1/2008 |
| KR | 10-0794702 B1 | 1/2008 |
| KR | 10-1108428 B1 | 1/2012 |
| KR | 10-2012-0022764 A | 3/2012 |
| KR | 10-1292714 B1 | 8/2013 |
| KR | 10-1411144 B1 | 6/2014 |
| KR | 10-1426275 B1 | 8/2014 |
| KR | 10-2016-0098955 A | 8/2016 |

(Continued)

OTHER PUBLICATIONS

15744328 Sequence Listing. (Year: 2020).*
15744328 NCBI Blast search JBD301 Description. (Year: 2020).*
15744328 NCBI Blast search JBD302 Description. (Year: 2020).*
15744328 NCBI Blast search JBD303 Description. (Year: 2020).*
15744328 NCBI Blast search JBD304 Description. (Year: 2020).*
15744328 NCBI Blast search JBD305 Description. (Year: 2020).*
15744328 NCBI Blast search JBD306 Description. (Year: 2020).*
15744328 NCBI Blast search JBD307 Description. (Year: 2020).*
15744328 NCBI Blast search JBD308 Description. (Year: 2020).*
15744328 NCBI Blast search JBD309 Description. (Year: 2020).*
15744328 NCBI Blast search JBD311 Description. (Year: 2020).*
15744328 NCBI Blast search JBD312 Description. (Year: 2020).*

(Continued)

*Primary Examiner* — Soren Harward
*Assistant Examiner* — Paul D Pyla
(74) *Attorney, Agent, or Firm* — Sughrue Mion, PLLC

(57) ABSTRACT

Provided are gut microbes or cultures having anti-obesity efficacy and a pharmaceutical composition containing them. The gut microbes or cultures have anti-obesity efficacy by lowering fatty acid concentration of the gut fluid contents in a mammalian gastrointestinal tract for the prevention and treatment of obesity and obesity related diseases. This invention demonstrated that said gut microbes having anti-obesity efficacy by lowering fatty acid concentration of the gut fluid contents in the gastrointestinal tract of mammals have the anti-obesity efficacy as much as that of the representative anti-obesity drug, orlistat, without any side effects in animal experiments and clinical trials. Therefore, the gut microbes h can be used to develop universal anti-obesity drugs for obese patients, contributing greatly to the health of mankind.

5 Claims, 12 Drawing Sheets

Specification includes a Sequence Listing.

(56) References Cited

FOREIGN PATENT DOCUMENTS

WO 2006/019222 A1 2/2006

OTHER PUBLICATIONS

15744328 NCBI Blast search JBD313 Description. (Year: 2020).*
15744328 NCBI Blast search JBD314 Description. (Year: 2020).*
15744328 NCBI Blast search JBD315 Description. (Year: 2020).*
Jeonbuk Daily, "Biotechnology Industry CEO Jeon, Kim, Hyunjin Biotechnology Field Market Leader", URL: http://www.jjan.kr/news/articleView.htm, Oct. 26, 2014, 5 pages.
Hea-Jong Chung et al., "Intestinal removal of free fatty acids from hosts by Lactobacilli for the treatment of obesity" FEBS Open Bio, Jan. 18, 2016, pp. 64-76, vol. 6, No. 1.
Jun Goo Kang et al., "Anti-Obesity Drugs: A Review about their Effects and Safety", Diabetes and Metabolism Journal, 2012, pp. 13-25, vol. 36.
Peter J. Turnbaugh et al., "An obesity-associated gut microbiome with increased capacity for energy harvest", Nature, Dec. 21/28, 2006, pp. 1027-1031, vol. 444.
Andrew L. Kau et al., "Human nutrition, the gut microbiome and the immune system", Nature, Perspective, Jun. 16, 2011, pp. 327-336, vol. 474.
Patrice D. Cani et al., "The Role of the Gut Microbiota in Energy Metabolism and Metabolic Disease", Current Pharmaceutical Design, 2009, pp. 1546-1558, vol. 15, No. 13.
Office Action issued from Korean Patent Office issued in counterpart Application No. 10-2015-0156733 dated Jan. 25, 2018.
International Search Report for PCT/KR2016/012791 dated Feb. 15, 2017 [PCT/ISA/210].

* cited by examiner

[FIG. 3A]
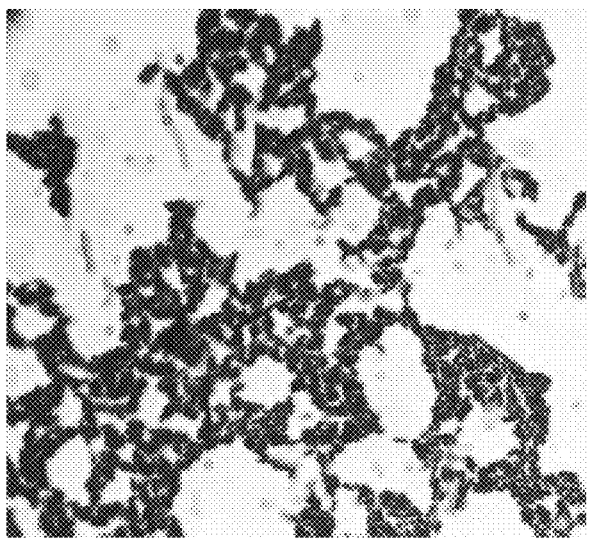
[FIG. 3B]
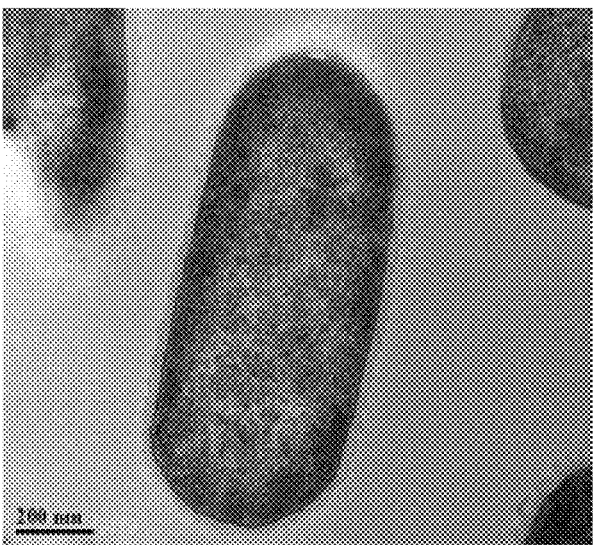

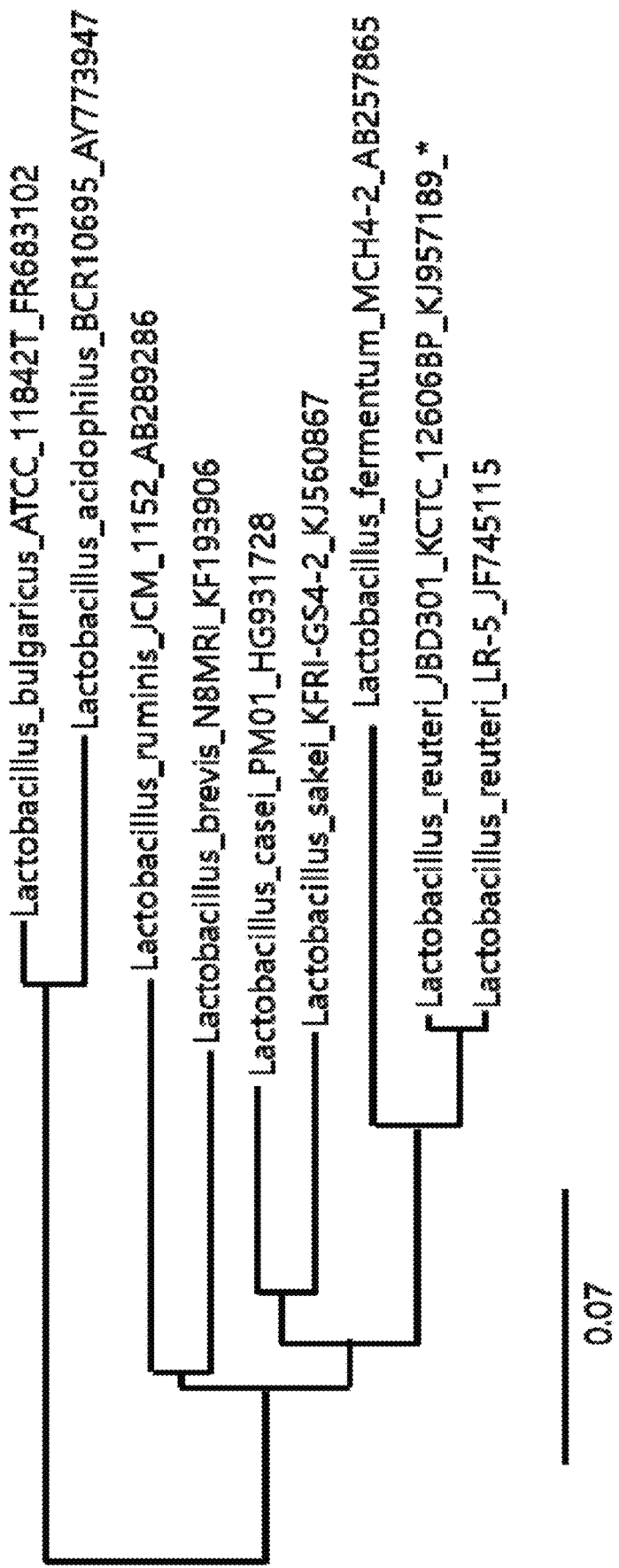
[FIG. 4]

[FIG. 8]
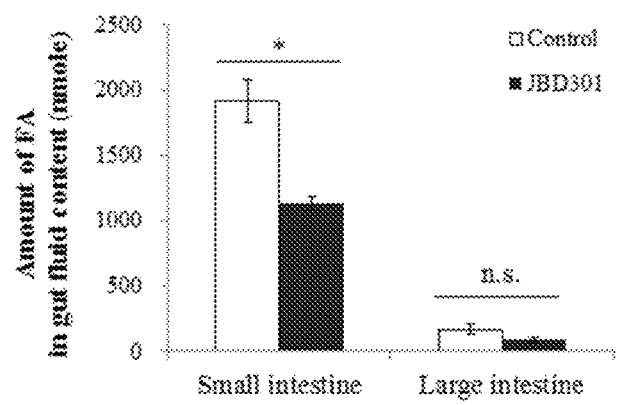
[FIG. 9]
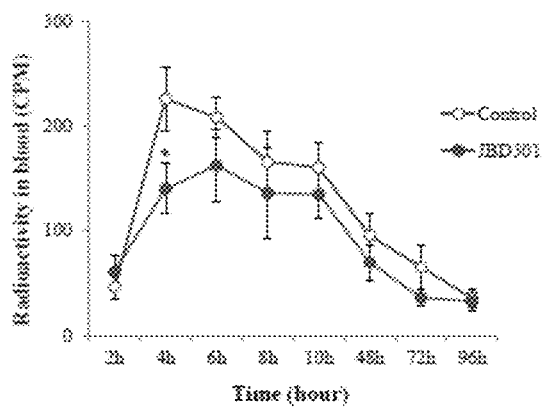

[FIG. 10]
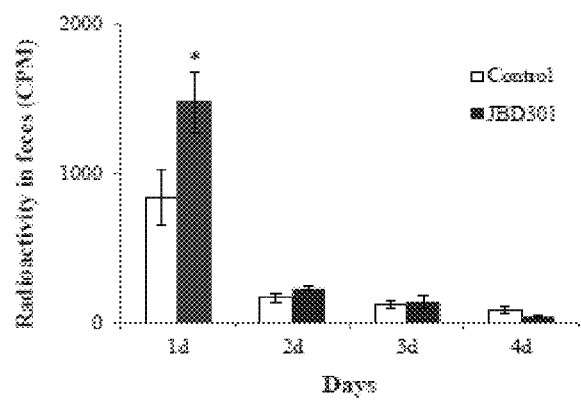
[FIG. 11]
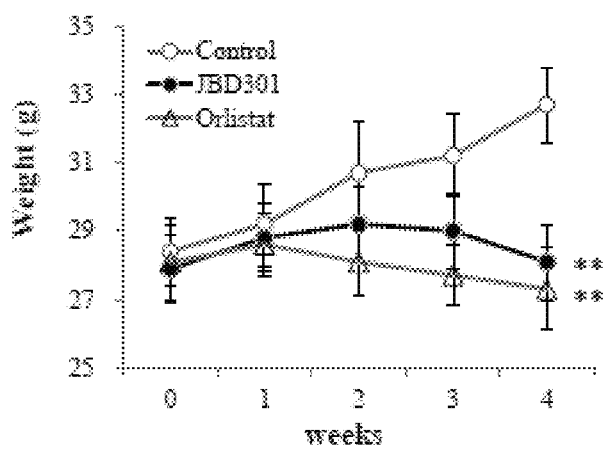

[FIG. 12]
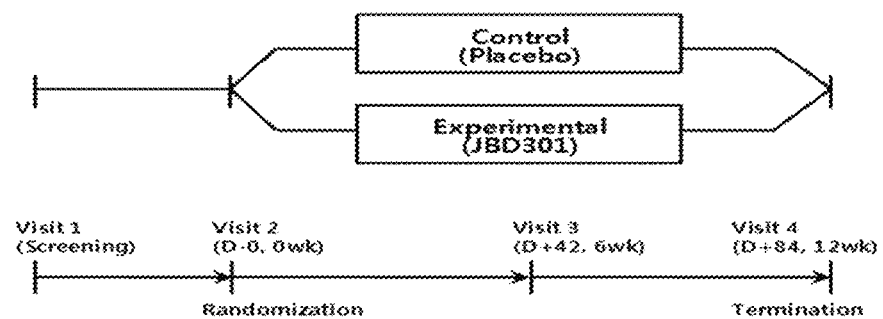

STRAIN HAVING ABILITY TO INHIBIT OBESITY AND PHARMACEUTICAL COMPOSITION CONTAINING SAME

CROSS REFERENCE TO RELATED APPLICATIONS

This application is a National Stage of International Application No. PCT/KR2016/012791 filed Nov. 8, 2016, claiming priority based on Korean Patent Application No. 10-2015-0156733 filed Nov. 9, 2015, the contents of all of which are incorporated herein by reference in their entirety.

TECHNICAL FIELD

The present application relates to novel microorganisms having anti-obesity ability and pharmaceutical composition containing the same, particularly relates to novel gut microbes having anti-obesity efficacy by lowering fatty acid concentration and/or reducing fatty acid amounts of the gut fluid contents in a mammalian gastrointestinal tract for the prevention and treatment of obesity and obesity related diseases.

BACKGROUND ART

Obesity is an epidemic disease that is rarely curable and is increasing in prevalence in most of the world. It poses a major risk for various serious chronic diseases, such as metabolic syndrome, hypertension, type II diabetes, dyslipidemia, arteriosclerosis, ischemic heart disease, fatty liver disease, gallstones etc.

Because obesity is itself serious disease and causes cosmetic issues, intensive research has been conducted to develop anti-obesity pharmaceutical drugs. The main prescription products currently approved for obesity belongs to appetite suppressants or lipid digestion inhibitors.

Anti-obesity drugs through appetite suppression, such as fenfluramine, sibutramine, rimonabant, phentermine, acts on central nervous system, controlling appetite and therefore decreasing food intake. While appetite suppression drugs show great anti-obesity efficacy, many were withdrawn from the market due to severe side effects associated with sympathomimetic properties. Fenfluramine that led early anti-obesity market was discontinued in 1997 due to affection in heart rate and blood pressure. Also sibutramine (Meridia®, Reductil®) was discontinued in 2009 due to side effects such as increased heart rate. Rimonabant (Acomplia®, Sanofi-Aventis), launched in Europe, was discontinued in 2008 due to problems of serious mental illness such as depression and suicide. Recently, new anti-appetite drugs, phentermine/topiramate (Qsymia®) and lorcaserin (Belviq®), have been approved by FDA but its continuous marketing is not guaranteed since these anti-appetite drugs cannot avoid the occurrence of serious side effects after long-term use (Diabetes Metab J 2012; 36:13-25).

Orlistat (Xenical® and Alli® of Roche) is the only anti-obesity drug marketed successfully among lipid digestion inhibitor drugs for obesity. Orlistat is a gastric and pancreatic lipase inhibitor that prevents fat hydrolysis. Thus, administration of orlistat results in inhibition of fat digestion, reducing dietary fat absorption into the body but increasing fat excretion from the body. However, undigested fat along the gastrointestinal tract causes side effects such as diarrhea and fatty stool, which is not only uncomfortable but also socially unacceptable. Moreover, some report that long-term use of orlistat causes serious liver toxicity, causing US FDA review the safety of orlistat.

In conclusion, currently available anti-obesity drugs are not ideal and the social demand for obesity treatment that can treat obesity effectively without side effects is very high. Consequently, anti-obesity drugs with different modes of action without side effects are under active investigation all over the world. The most interesting approach among drug development through new paradigm is anti-obesity drugs using gut microbiota.

Obesity has been thought as a disease of energy balance, characterized by a chronic disequilibrium between energy intake and expenditure. Recent evidence showed that the gut microbiota plays an intricate role in the regulation of body weight and obesity (Nature 444:1027-31, Nature 474:327-36). The human digestive tract contains a complex diversity of bacteria, with over $10^{14}$ microbes which is more than 10 times of human cell numbers, interacting with human cells. Through interaction with human cells, gut microbes regulate absorption of food to human body and thus regulate the body weight and obesity of host. Theoretically, gut microbes have a tremendous advantage of excellent safety since they stay symbiotically in the intestine without being absorbed into the body. Thus, many efforts have been made to develop gut microbes as anti-obesity drugs with new mode of action (Current Pharmaceutical Design, 2009, 15:1546-1558).

U.S. Pat. No. 8,257,695 by Dupont provides satiety microbes, *Lactobacillus acidophilus* PTA 4797, *Bacillus lactis* 420, *Bacillus lactis* HN019 and *Lactobacillus salivarius* Ls-33 as anti-obesity agents.

U.S. Pat. No. 8,454,949 and 200601922 by Nestec provides t10c12-octadecadienoic acid producing *Lactobacillus rhamnosus* CNCM I-4046, U.S. Pat. Nos. 8,440,178 and 8,318,151 provides *Lactobacillus rhamnosus* NCC4007, U.S. Pat. No. 8,318,150 provides *Lactobacillus helveticus* CNCM I-4095, U.S. Pat. No. 8,637,000 provides *Lactobacillus rhamnosus* (ATCC53103), and EU Patent 2123168 provides *Lactobacillus paracasei* CNCM I-2116 as anti-obesity microbes.

U.S. Pat. No. 8,440,179 by Megamilk Snow Brand provides *Lactobacillus gasseri* SBT2055 and *Lactobacillus helveticus* SBT2171 as fat-reducing agents.

U.S. Pat. No. 7,001,756 by Genmont Niotech provides *Lactobacillus rhamnosus* GM-020 as anti-obesity agents. US patent 2009-0181437 by Yakult provides the conjugation method of linoleic acid to conjugated linoleic acid (CLA) and strains for that.

KR 2006-019222, EU Patent 1789531 and US Patent 2008-0267932 by CJ provides *Lactobacillus rhamnosus* PL60 (KCCM-10654P), converting linoleic acids to conjugated linoleic acid (CLA), as anti-obesity agents. US Patent 2008-0057044 by CJ provides *Lactobacillus plantarum* PL62 (KCCM-10655P), as anti-obesity agents.

KR Patent 543114 by Yakult provides *Bacillus subtilis* KY912 (KACC-91056) producing metabolites which inhibits α-glucosidase activity, as anti-obesity microbes. KR Patent 404236 by Bioneer provides *Acetobacter* sp. BC-Y058 and *Lactobacillus* sp. BC-Y009 which convert mono- and di-saccharides in the gut to polysaccharides for the prevention and treatment of diabetes and obesity. Bioneer also provides polysaccharide-producing *Lactobacillus reuteri* (KCTC-10301BP) in KR Patent 794701, *Lactobacillus fermentum* NM316 (KCTC-10458BP) in KR Patent 794702, and *Lactobacillus gasseri* BNR17 (KCTC 10902BP) in KR Patent 1108428.

Also, JINIS biopharmaceuticals, the assignee of this invention, provides fatty-acid absorbing *Lactobacillus aci-*

*dophilus* FARM1 (KCTC 11513BP), FARM2 (KCTC 11514BP) and FARM3 (KCTC 11515BP) as anti-obesity agents in KR Patent 1292714.

However, all these anti-obesity microbes were effective in animal experiments but failed to successfully commercialized due to ineffective treatment and/or prevention in clinical trials.

DISCLOSURE OF INVENTION

Technical Problem

Currently available anti-obesity drugs are chemical-based pharmaceuticals but not ideal with serious side effects. To solve this unmet need, research teams around the world are developing therapeutic agents for obesity using intestinal microorganisms. So far, however, all these anti-obesity microbes only demonstrate the possibility of treating obesity without side effects without success to develop pharmaceutical drugs using anti-obesity microbes.

Previous studies on the anti-obesity drug development using gut microbes have shown treatment in which gut microbes can control the satiety in the body, overproduce certain metabolites with anti-obesity effect, inhibit glycolysis, convert monosaccharides to polysaccharides, convert the general nutritional ingredients into anti-obesity substances (bioconversion) or promotes polysaccharide production. However, previous animal experiments and clinical trials only show that all these approaches were not effective to treat obesity.

Orlistat is the only anti-obesity drug approved for long-term use by healthcare departments of governments around the world. Orlistat, secreted into the gut content, is a pancreatic lipase inhibitor that prevents fat hydrolysis. Thus, administration of orlistat results in inhibition of fat digestion by inhibition of pancreatic lipase, reducing digestion of fat into absorbable fatty acids in the gut for obesity treatment. Based on this scientific observation, we have acknowledged that lowering the concentration of fatty acids in the gut fluid content using gut microbes can treat obesity as effective as orlistat. Unlike orlistat which cannot be free of side effect due to its property as chemicals, gut microbes have a tremendous advantage of inherent safety without side effect since they stay symbiotically in the intestine. Moreover, orlistat causes indigestion due to lipase inhibition activity while gut microbes specifically remove fatty acids in the gut without indigestion problem.

One object of this invention is to provide gut microbes having anti-obesity efficacy by lowering fatty acid concentration and/or reducing fatty acid amounts of the gut fluid contents in the gastrointestinal tract of mammals.

Another object of this invention is to provide functional foods and pharmaceuticals containing above microbes or cultures to prevent or treat obesity or obesity-related diseases.

Technical Solution

To accomplish the said objects, the present invention provides novel gut microbes having anti-obesity efficacy by lowering fatty acid concentration and/or reducing the amount of fatty acids of the gut fluid contents in the gastrointestinal tract of mammals.

The present invention also provides pharmaceuticals containing above microbes or cultures having anti-obesity efficacy by lowering fatty acid concentration and/or reducing fatty acid amounts of the gut fluid contents in the gastrointestinal tract of mammals to prevent or treat obesity and obesity-related diseases.

The present invention also provides functional foods containing above microbes or cultures having anti-obesity efficacy by lowering fatty acid concentration and/or reducing fatty acid amounts of the gut fluid contents in the gastrointestinal tract of mammals to prevent or treat obesity and obesity-related diseases.

In this invention, said gut microbes can be selected from the groups that include, but are not limited to, *Lactobacillus* species, *Streptococcus* species, and *Lactococcus* species.

In this invention, said *Lactobacillus* species can be selected from the groups that include, but are not limited to, *Lactobacillus reuteri, Lactobacillus plantarum, Lactobacillus casei, Lactobacillus paracasei, Lactobacillus alimentarius, Lactobacillus delbrueckii* subsp. *Lactis, Lactobacillus pantheris, Lactobacillus fermentum, Lactobacillus rhamnosus, Lactobacillus salivarius* subsp. *salicinius, Lactobacillus mali.* and said *Streptococcus* species can be selected from the groups that include, but are not limited to, *Streptococcus lutetiensis*, and said *Lactococcus* species can be selected from the groups that include, but are not limited to, *Lactococcus lactis* subsp. *Lactis.*

In this invention, said *Lactobacillus* species can be selected from the groups that include, but are not limited to, *Lactobacillus reuteri* JBD301 (KCTC 12606BP), *Lactobacillus plantarum* JBD302 (KCTC 12918BP), *Lactobacillus casei* JBD303 (KCTC 12919BP), *Lactobacillus casei* JBD304 (KCTC 12920BP), *Lactobacillus paracasei* JBD305 (KCTC 12921BP), *Lactobacillus alimentarius* JBD306 (KCTC 12922BP), *Lactobacillus delbrueckii* subsp. *Lactis* JBD307 (KCTC 12923BP), *Lactobacillus pantheris* JBD308 (KCTC 12924BP), *Lactobacillus fermentum* JBD309 (KCTC 12925BP), *Lactobacillus rhamnosus* JBD311 (KCTC 12926BP), *Lactobacillus salivarius* subsp. *salicinius* JBD312 (KCTC 12927BP) and *Lactobacillus mali* JBD313 (KCTC 12928BP), said *Streptococcus* species can be selected from the groups that include, but are not limited to, *Streptococcus lutetiensis* JBD314 (KCTC 12929BP), and said *Lactococcus* species can be selected from the groups that include, but are not limited to, *Lactococcus lactis* subsp. *Lactis* JBD315 (KCTC 12930BP).

[Benefits]

This invention demonstrated that said gut microbes having anti-obesity efficacy by lowering fatty acid concentration and/or reducing the amount of fatty acids of the gut fluid contents in the gastrointestinal tract of mammals show the anti-obesity efficacy as much as that of the representative anti-obesity drug, orlistat, without any side effects in animal experiments and clinical trials.

Therefore, said gut microbes having anti-obesity efficacy by lowering fatty acid concentration and/or reducing the amount of fatty acids of the gut fluid contents in the gastrointestinal tract of mammals can be used to develop universal anti-obesity drugs for obese patients, contributing greatly to the health of mankind.

BRIEF DESCRIPTION OF THE DRAWINGS

FIG. 3A and FIG. 3B represent the gram staining images (FIG. 3A) and Transmission Electron Microscopy (TEM)

images (FIG. 3B) of said anti-obesity microbes *Lactobacillus reuteri* JBD301 (KCTC 12606BP).

FIG. 4 presents the phylogenic tree of said anti-obesity microbes *Lactobacillus reuteri* JBD301 (KCTC 12606BP), identified by the screening by the method in Example 1.

Figure 5A:
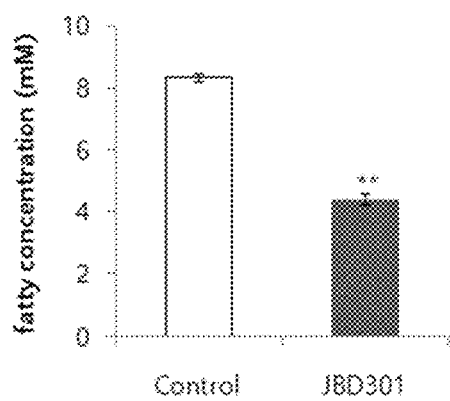
Figure 5B:
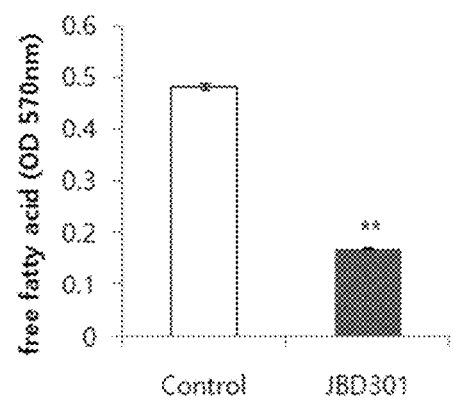
Figure 5C:
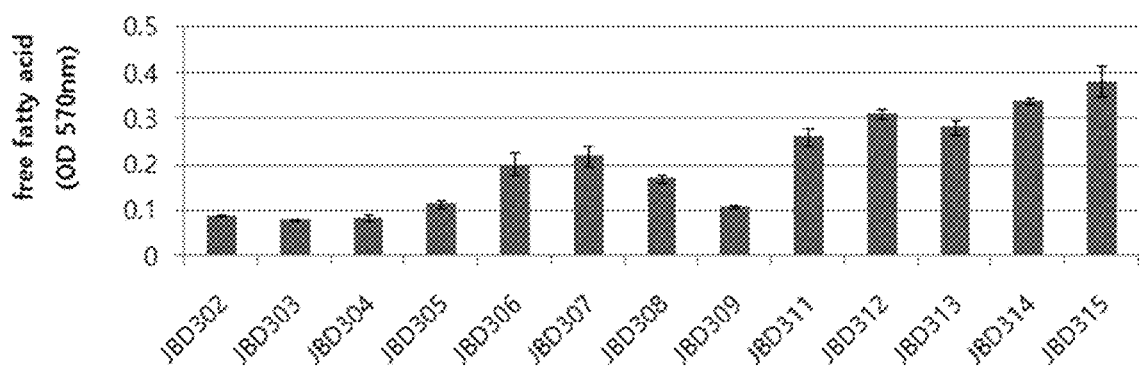

FIGS. 5A, 5B and 5C represent the capacity of lowering fatty acid concentration in vitro with the said anti-obesity microbes.

Figure 6:
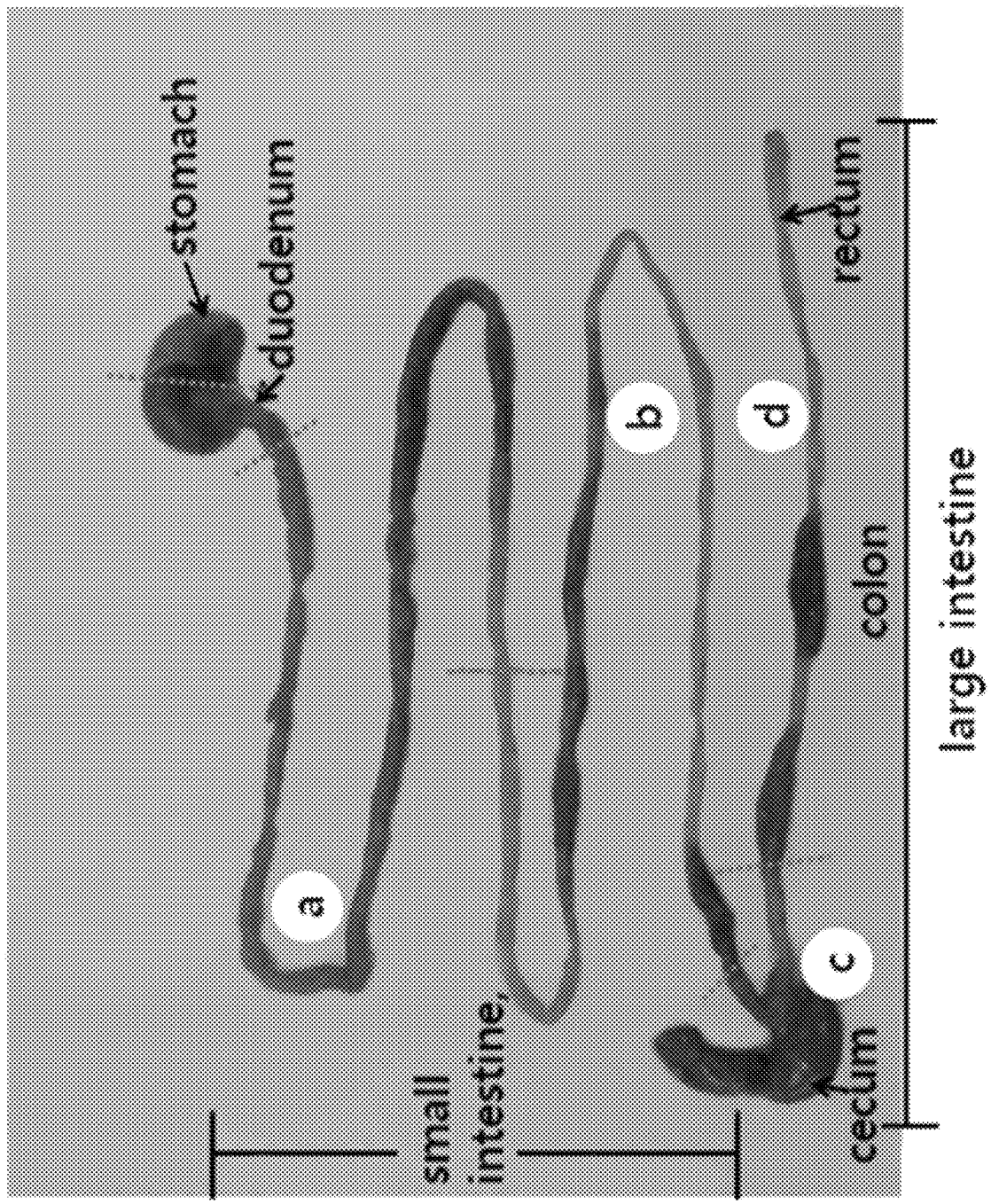

FIG. 6 presents the images of small intestine and large intestine used to measure the fatty acid concentration in the gut fluid contents of the host administered the said anti-obesity *Lactobacillus reuteri* JBD301 (KCTC 12606BP).

Figure 7:
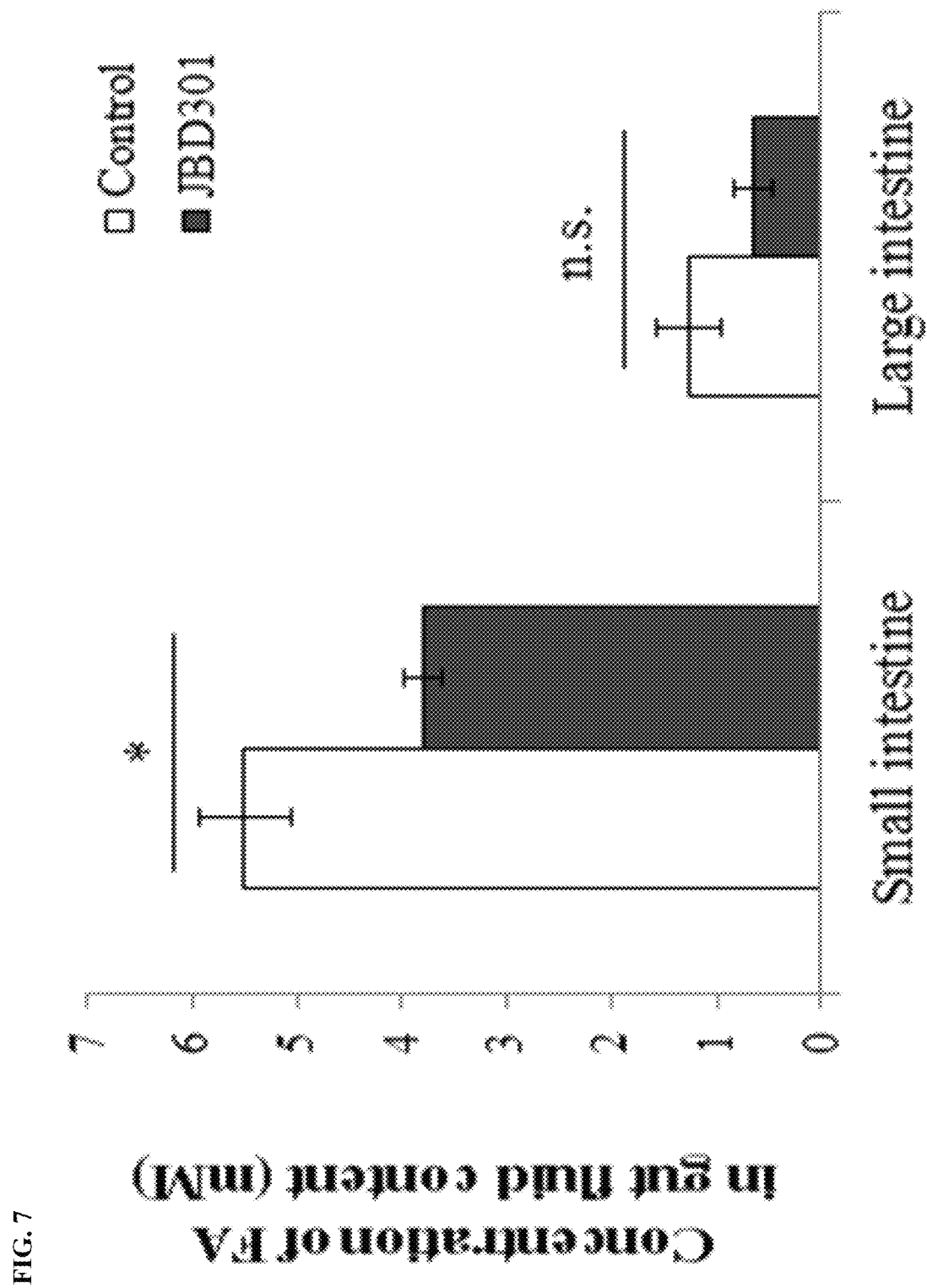

FIG. 7 presents the fatty acid concentration in the gut fluid contents of the host administered the said anti-obesity *Lactobacillus reuteri* JBD301 (KCTC 12606BP)(white: control, black: JBD301).

FIG. 8 presents the fatty acid amount in the gut fluid contents of the host administered the said anti-obesity *Lactobacillus reuteri* JBD301 (KCTC 12606BP)(white: control, black: JBD301).

FIG. 9 presents the absorbed amount of dietary fatty acids into the host administered the said anti-obesity *Lactobacillus reuteri* JBD301 (KCTC 12606BP)(white: control, black: JBD301).

FIG. 10 presents the excreted amount of dietary fatty acids from the host administered the said anti-obesity *Lactobacillus reuteri* JBD301 (KCTC 12606BP)(white: control, black: JBD301).

FIG. 11 presents the body weight changes of the host administered the said anti-obesity *Lactobacillus reuteri* JBD301 (KCTC 12606BP) following the method in Example 2 (○: control, •: JBD301, Δ: orlistat).

FIG. 12 presents clinical trial design for efficacy of said anti-obesity *Lactobacillus reuteri* JBD301 (KCTC 12606BP) following the method in Example 3.

Figure 13:
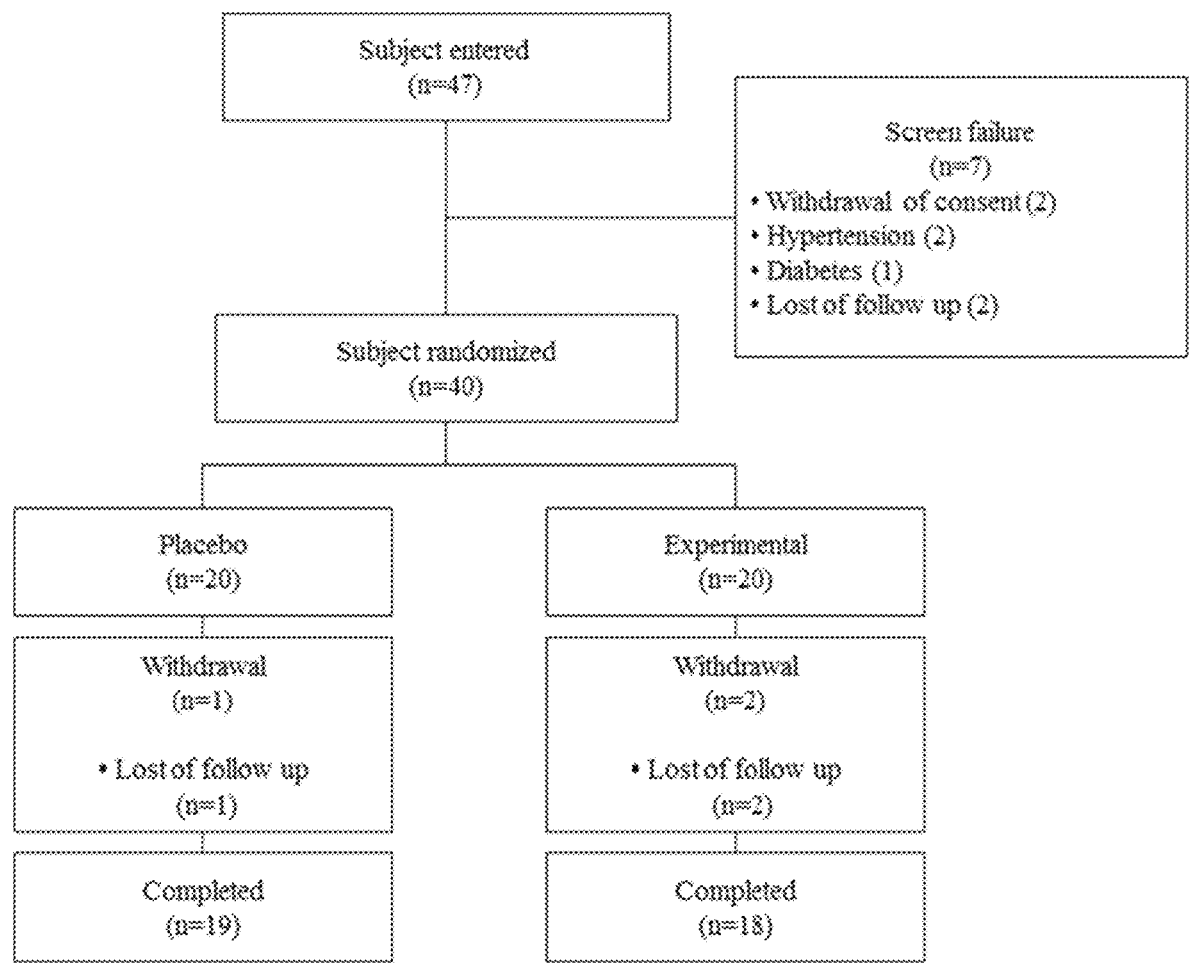

FIG. 13 presents the assignment of control and experimental for subjects screened in this trial for efficacy of said anti-obesity *Lactobacillus reuteri* JBD301 (KCTC 12606BP) following the method in Example 3.

Figure 14:
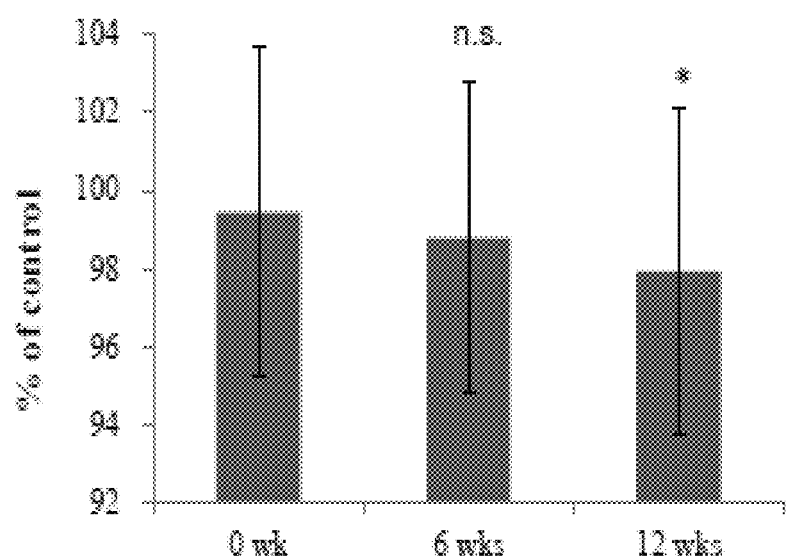

FIG. 14 presents the result of clinical trial for efficacy of said anti-obesity *Lactobacillus reuteri* JBD301 (KCTC 12606BP) following the method in Example 3.

DETAILED DESCRIPTION OF PREFERRED EMBODIMENTS

The currently available anti-obesity drugs have side effects or safety problems for long-term use. Previous attempts to develop safe anti-obesity drugs using appetite suppressant or lipase inhibitors have failed although the development is very urgent due to serious abuse problems with anti-obesity drugs.

Based on the understanding that previous anti-obesity drugs are absorbed into the body and causes various side effects due to the loss of appetite and inhibition of lipase inhibition, we attempted to confirm that symbiotic intestinal microorganisms that can reduce the fat absorption of the host can reduce obesity by reducing calorie intake.

Thus, in this invention, we conformed that 1) novel anti-obesity microbes were identified by screening intestinal microorganisms in the gastrointestinal tract, 2) novel anti-obesity microbes were colonized in the gastrointestinal tract of administered host, 3) novel anti-obesity microbes lowered the fatty acid concentration in the gut fluid content of host, 4) novel anti-obesity microbes reduced the absorption of dietary fat into the host but increase the secretion from the host, 5) novel anti-obesity microbes reduced the body weight of host.

Therefore, in the first aspect, the present invention relates to the gut microbes having anti-obesity efficacy by lowering fatty acid concentrations of the gut fluid contents in the gastrointestinal tract of mammals.

In this invention, said gut microbes can be selected from the groups that include, but are not limited to, *Lactobacillus* species, *Streptococcus* species, and *Lactococcus* species.

In this invention, said *Lactobacillus* species can be selected from the groups that include, but are not limited to, *Lactobacillus reuteri*, *Lactobacillus plantarum*, *Lactobacillus casei*, *Lactobacillus paracasei*, *Lactobacillus alimentarius*, *Lactobacillus delbrueckii* subsp. *Lactis*, *Lactobacillus pantheris*, *Lactobacillus fermentum*, *Lactobacillus rhamnosus*, *Lactobacillus salivarius* subsp. *salicinius*, *Lactobacillus mali*. and said *Streptococcus* species can be selected from the groups that include, but are not limited to, *Streptococcus lutetiensis*, and said *Lactococcus* species can be selected from the groups that include, but are not limited to, *Lactococcus lactis* subsp. *Lactis*.

In this invention, said *Lactobacillus* species can be selected from the groups that include, but are not limited to, *Lactobacillus reuteri* JBD301 (KCTC 12606BP), *Lactobacillus plantarum* JBD302 (KCTC 12918BP), *Lactobacillus casei* JBD303 (KCTC 12919BP), *Lactobacillus casei* JBD304 (KCTC 12920BP), *Lactobacillus paracasei* JBD305 (KCTC 12921BP), *Lactobacillus alimentarius* JBD306 (KCTC 12922BP), *Lactobacillus delbrueckii* subsp. *Lactis* JBD307 (KCTC 12923BP), *Lactobacillus pantheris* JBD308 (KCTC 12924BP), *Lactobacillus fermentum* JBD309 (KCTC 12925BP), *Lactobacillus rhamnosus* JBD311 (KCTC 12926BP), *Lactobacillus salivarius* subsp. *salicinius* JBD312 (KCTC 12927BP) and *Lactobacillus mali* JBD313 (KCTC 12928BP), said *Streptococcus* species can be selected from the groups that include, but are not limited to, *Streptococcus lutetiensis* JBD314 (KCTC 12929BP), and said *Lactococcus* species can be selected from the groups that include, but are not limited to, *Lactococcus lactis* subsp. *Lactis* JBD315 (KCTC 12930BP).

In a preferred embodiment of the invention, said gut microbes can be any microbes derived from human gut microbiota or gastrointestinal tract of mammals, can be in mammalian gastrointestinal tract, can lower the fatty acid concentrations in the gut fluid content of gastrointestinal tract, thereby reducing the absorption of dietary fat to the host.

Preferably, said gut microbes show the following 4 characteristics that can help to solve the side effect problems with the current anti-obesity drugs.

First, said gut microbes are not absorbed into the body but colonize in the gut and therefore there is no side effects caused by the absorption as in the case of chemical-based anti-obesity drugs. Second, said gut microbes are not acting on central nervous system and therefore there is no side effects caused by abuse or long-term use as in the case of appetite suppression drugs. Third, said gut microbes are not acting on fat digestion and therefore there is no side effects such as diarrhea, fatty stool, indigestion as in the case of lipase inhibition drugs. Forth, said gut microbes are safe and beneficial microorganisms and belongs to GRAS category.

In another aspect, the present invention relates to pharmaceutical compositions containing a gut microbe or culture with anti-obesity efficacy by lowering fatty acid concentrations in the gut fluid contents of in a mammalian gastrointestinal tract for the prevention or treatment of obesity or metabolic diseases caused by obesity.

In another aspect, the present invention relates to functional food composition containing a gut microbe or culture with anti-obesity efficacy by lowering fatty acid concentrations in the gut fluid contents of in a mammalian gastrointestinal tract for the prevention or treatment of obesity or metabolic diseases caused by obesity.

Preferably, said microbes or cultures contained in pharmaceutical or functional food compositions can lower fatty acid concentrations of the gut fluid contents more than 5%, and said gut may include stomach, small intestine and large intestine.

Preferably, said microbes or cultures may be contained, but not restricted, at dose of $10^3$~$10^{12}$ cfu/gram in pharmaceutical or functional food compositions.

In this invention, said pharmaceutical compositions could be formulated, but not limited to, with more than 1 kind of pharmaceutically acceptable carrier in addition to said microbes or cultures having anti-obesity efficacy by lowering fatty acid concentrations of the gut fluid contents in the gastrointestinal tract.

In this invention, said functional foods are foods supplemented with functional ingredients and include, but not limited to, health food, nutraceuticals, dietary supplement, pharmabiotics. Preferably, said functional ingredients is for prevention and/or treatment of obesity and related metabolic syndrome.

Said functional foods include, but not limited to, dairy food (milk, soy milk, processed milk), fermented milk (drinking yogurt, set curd yogurt), drink, and soda. Said functional foods can include various supplementary components in addition to the functional ingredients. In the case of the functional food of the present invention, it is preferable to use additional supplements that include, but not limited to, vegetable creamer, skim milk powder, sugar, vitamin A, vitamin B1, vitamin B2, vitamin B3, vitamin B6, vitamin B12, folic acid, vitamin C, vitamin D3, Vitamins, and minerals such as copper, calcium, iron, magnesium, potassium, and zinc. In addition, said functional foods of the present invention may contain various flavors or natural carbohydrates as additional components as in the case of ordinary beverages. Said flavor agents may include natural sweeteners such as thaumatin and stevia extract, and synthetic sweeteners such as saccharin and aspartame. Said natural carbohydrates may include monosaccharides such as glucose and fructose, disaccharides such as maltose and sucrose, polysaccharides such as dextrin and cyclodextrin, and sugar alcohols such as xylitol, sorbitol and erythritol.

Said pharmaceuticals and functional foods in this invention contain said gut microbes having anti-obesity efficacy, and thus the administration of said pharmaceuticals and functional foods reduce the absorption of dietary fat into the host, contributing the prevention and/or treatment of obesity and related metabolic syndromes.

The technical idea of the present invention for the treatment of obesity can be applied to any gut microbes with anti-obesity efficacy by lowering fatty acid concentrations of the gut fluid contents in the gastrointestinal tract of mammals and will be apparent to those skilled in the art to which the present invention pertains.

EXAMPLES

The present invention may be better understood with reference to the accompanying examples that are intended for purposes of illustration only and should not be construed to limit the scope of the invention, as defined by the claims appended hereto.

Example 1: Screening for Anti-Obesity Gut Microbes

Figure 1A:
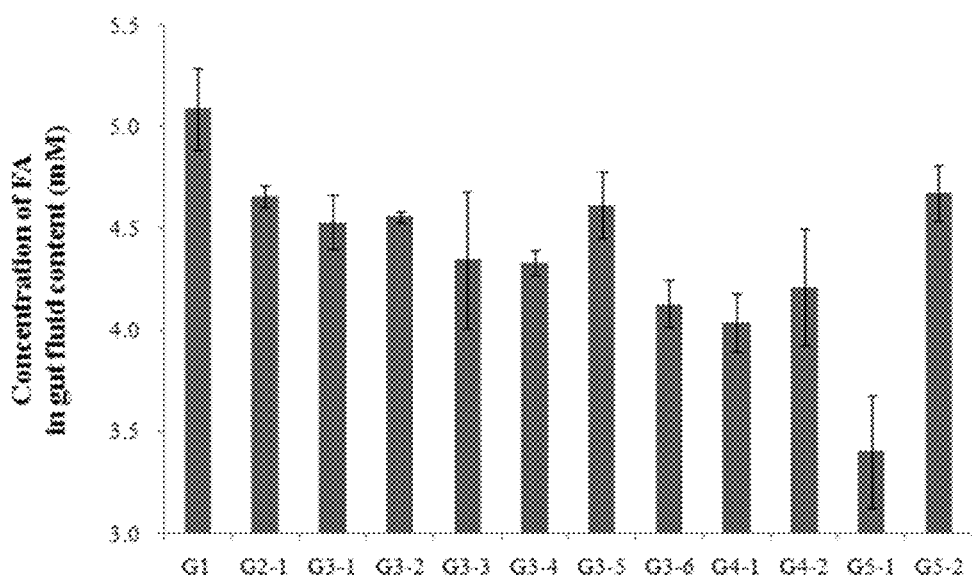
FIGS. 1A and 1B and FIGS. 2A and 2B present the fatty acid concentration in the gut fluid contents 1A and 2A and body weight changes 1B and 2B of the host administered the said anti-obesity microbes following the method in Example 1.
Figure 1B:
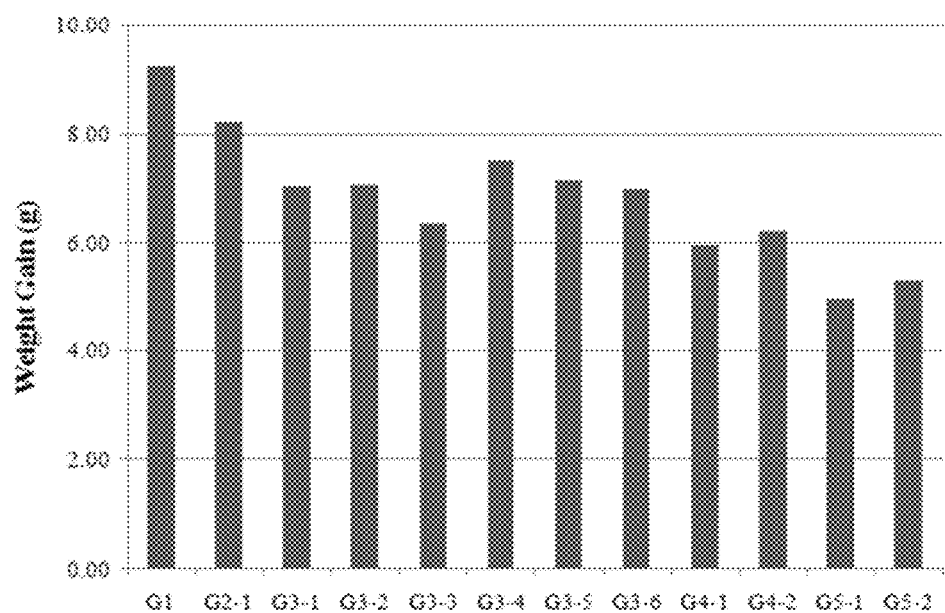
Figure 2A:
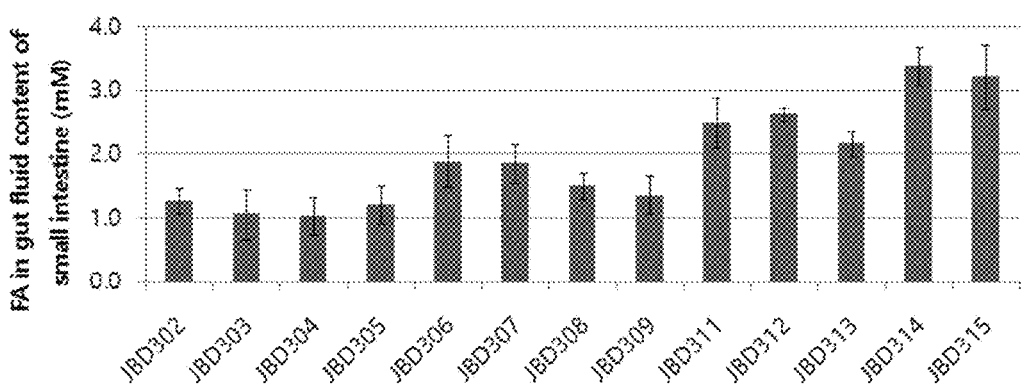
Figure 2B:
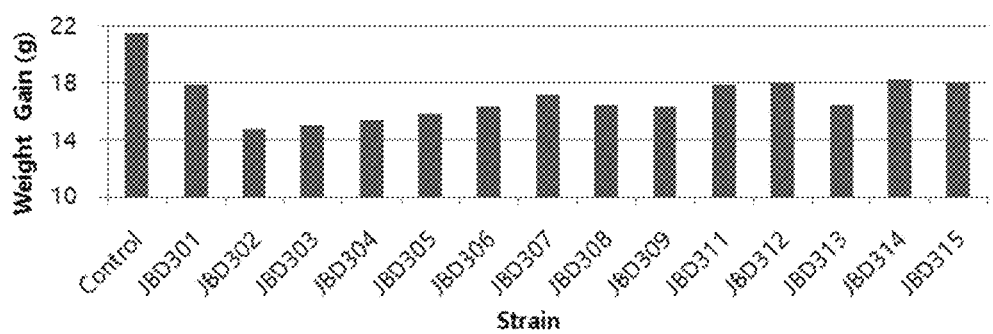

By screening more than 20,000 strains with the said methods, we were able to find various gut microbes that can lower fatty acid concentration, followed by administration into mice for 12 weeks to measure the fatty acid concentration in the gut fluid contents and body weight changes of the host, as shown in FIGS. 2A and 2B.

Experiment 1. Identification of Anti-Obesity Gut Microbes

The anti-obesity gut microbes, G5-1(JBD301), JBD302JBD309, JBD311-JBD315, were identified by screening as in Example 1. The taxonomic classification and phylogenetic analysis were based on the 16S rDNA gene and morphological observations. For morphological analysis, freshly cultured *Lactobacillus* was used for standard light microscopy after Gram staining as well as Transmission Electron Microscopy (TEM). FIGS. 3A and 3B shows morphology of G5-1(JBD301), confirming G5-1 as gram (+) *bacillus*.

For 16S rRNA analysis, DNA was extracted from a G5-1 culture. For amplification of the 16s rDNA, PCR was performed in an automated thermal cycler with an initial denaturation at 95° C. for 5 min, followed by 30 cycles at 95° C. for 30 sec, 52° C. for 45 sec, 72° C. for 2 min, and then 72° C. for 10 min. For amplification of the 16s rDNA, universal primers (SEQ ID NO: 1 and SEQ ID NO: 2) were selected

[SEQ ID NO: 1] 27 F: 5'-AGA GTT TGA TCC TGG CTC AG-3'

[SEQ ID NO: 2] 1492R: 5'-GGT TAC CTT GTT ACG ACT T-3'

The obtained 16s rDNA sequences (SEQ ID NOS: 3-16) of G5-1(JBD301), JBD302-JBD309, and JBD311-JBD315 were used to identify homologous sequences by searching the NCBI GenBank, DNA data bank of Japan, European Nucleotide Archive. After confirming novel species of the above microbes, G5-1(JBD301) were deposited as NCBI GenBank Accession number KJ957189.

Experiment 2. Acid Production of Anti-Obesity Gut Microbes

To test acid production, JBD301 microbe was cultured at 37° C. in MRS broth. The cell culture was inoculated into bottles containing 100 ml of sterile reconstituted skim milk (10%) and glucose (2%). The pH changes of the fermented milk were determined after incubation for 24, 48 and 72 h. The average value with 10 samples per group was indicated as mean±standard deviation, as shown in Table 1.

TABLE 1

| Time (hr) | JBD 301-fermented yogurt pH |
|---|---|
| 24 | 4.404 ± 0.034 |
| 48 | 4.092 ± 0.059 |
| 72 | 4.048 ± 0.012 |

As shown in Table 1, pH reduction by acid production was observed.

Experiment 3. In Vitro Evaluation of Lowering Fatty Acid Concentration by Anti-Obesity Gut Microbes JBD301 was inoculated onto MRS agar for incubation at 37° C. in anaerobic jar (Gas-Pack anaerobic systems, BBL).

After 48 hours, colonies on MRS agar were inoculated into MRS media in 96-well plate for anaerobic incubation at 37° C. The obtained culture was subjected to EnzyChrom™ FFA Assay Kit (Bio-Assay Systems) as in Example 1. The amount of fatty acid in the supernatant was determined with EnzyChrom™ FFA Assay Kit (Bio-Assay Systems) using absorbance at 570 nm and the capacity of lowering fatty acid concentration by JBD301 was shown in FIGS. 5A, 5B and 5C.

As shown in FIGS. 5A, 5B and 5C, fatty acid concentration in the media of JBD301 group was 55% of the control, which is statistically significant (p=0.01). Also, fatty acid concentrations in the media of other JBD group, JBD302-JBD309, JBD311-JBD315 was also lowered than that of the control group.

Experiment 4. In Vivo Evaluation of Lowering Fatty Acid Concentration in the Gut Fluid Content by Anti-Obesity Gut Microbes

*Lactobacillus* colonize in the small intestine, where fatty acids, digestion products of lipid, are mainly absorbed in the body. The decrease in the amount of fatty acids in the small intestine where most of the fatty acid is absorbed reduces the amount of fat that can be absorbed by the human body, thus reducing the caloric intake of the host. To confirm this, the concentration and amount of fatty acids in the intestinal fluid (gut fluid content) were measured.

Six-week-old C57BL/6 female mice (Joongang Experimental Animal Co., Seoul, Korea) were housed at 7 animals per cage with food (10% fat; D12450B; Research Diets Inc., New Brunswick, N.J., USA) and water available ad libitum under a 12-h light/12-h dark cycle at 22° C. and 55% humidity. After 1 week of acclimation, mice were randomly divided into with control or experimental group. Control mice were fed high-fat diet (45% kcal as fat, D12451, Research Diets Inc.) while experimental mice fed high-fat diet supplemented daily with $10^7$ CFU of JBD301 for 3 weeks. After 3-week administration of *Lactobacillus*, mice were sacrificed under anesthesia. Both total fluid contents from small and large intestine were collected immediately and weighed. The gut fluid contents were collected with known volume of sterile saline. Then, the samples in saline were centrifuged at 10,000×g for 30 min. After centrifugation, the supernatant was collected and analyzed for total FFAs content using the EnzyChrom™ Free Fatty Acid Assay Kit (Bio-Assay Systems), as shown in FIGS. 7 and 8.

FIG. 6 shows the images of small intestine (a, b) and large intestine (c, d) used to measure the fatty acid concentration in the gut fluid content.

FIG. 7 presents the fatty acid concentration in the gut fluid contents of the host administered the said anti-obesity *Lactobacillus reuteri* JBD301 (KCTC 12606BP). The fatty acid concentration in the small intestine of JBD301 group was 69% of the control, which is statistically significant difference (p=0.022), while that in the large intestine was not much different (p=0.158).

FIG. 8 presents the fatty acid amount in the gut fluid contents of the host administered the said anti-obesity *Lactobacillus reuteri* JBD301 (KCTC 12606BP). The fatty acid amount in the small intestine of JBD301 group was 59% of the control, which is statistically significant difference (p=0.01), while that in the large intestine was not much different (p=0.153).

Experiment 5. In Vivo Evaluation of Lowering Fatty Acid Absorption and Increasing Fatty Acid Excretion by Anti-Obesity Gut Microbes To evaluate lowering of fatty acid absorption in the host after administration of JBD301, mice were fed high-fat diet supplemented with JBD301 for 3 weeks and then 14C-radiolabeled triolein was orally administered as in Experiment 4. Blood was collected at times (2 h~96 h), mixed with liquid scintillation cocktail, and radioactivity from 14C was measured with Microplate Scintillation Counter (PerkinElmer), as shown in FIG. 9.

FIG. 9 confirmed that the radioactivity of the blood in JBD301 group was decreased at all times compared to the control group. Particularly, it decreased down to 62% compared to that of the control, showing significant difference at 4 hours after intake of radiolabeled food (p=0.048).

Also, feces were collected to evaluate the excretion amount of fatty acid from the host after administration of JBD301. Fecal samples at times were added to Solvable™ (PerkinElmer), mixed for 1 hour at 60° C., and bead homogenized samples were centrifuged at 13,000 rpm for 5 minutes. Then, the supernatant was added with $\frac{1}{10}$ (v/v) $H_2O_2$, mixed for 10 minutes at 50° C. and centrifuged at 13,000 rpm for 5 minutes. The obtained supernatant was added with liquid scintillation cocktail and 14C radioactivity was measured with Microplate Scintillation Counter (PerkinElmer).

FIG. 10 shows the excreted amount of dietary fatty acids from the host administered the said anti-obesity *Lactobacillus reuteri* JBD301 (KCTC 12606BP). The radioactivity of the feces in JBD301 group was increased for 3 days compared to the control group. Particularly, it increased up to 177% compared to that of the control, showing significant difference (p=0.037).

Example 2. In Vivo Evaluation of Weight Control Efficacy by Anti-Obesity Gut Microbes All animal care and use were performed strictly in accordance with the ethical guidelines by the Institutional Animal Care and Use Committee. Six-week-old C57BL/6 female mice (Joongang Experimental Animal Co., Seoul, Korea) were housed at 10 animals per cage with food (10% fat; D12450B; Research Diets Inc., New Brunswick, N.J., USA) and water available ad libitum under a 12-h light/12-h dark cycle at 22° C. and 55% humidity. After 1 week of acclimation, mice were randomly divided into with control or experimental groups. Control mice were fed high-fat diet (45% kcal as fat, D12451, Research Diets Inc.), JBD301 group fed high-fat diet supplemented with $10^7$ CFU of JBD301, and orlistat group fed high-fat diet supplemented with orlistat (Xenical®, Roche) 50 mg/kg diet. Body weight changes were monitored for 4-week administration as shown in FIG. 11.

As shown in FIG. 11, there was clear weight reduction in diet-induced obese mice after daily administration of JBD301 at $1 \times 10^7$ CFU and the degree of anti-obesity efficacy by *Lactobacillus* JBD301 was as much as that of mice fed anti-obesity drug, orlistat.

Example 3. Clinical Trial to Evaluate Weight Control Efficacy by Anti-Obesity Gut Microbes Phase 2 clinical trials were performed to validate the efficacy of JBD301 as anti-obesity microbes (Clinical Research Information Service of Korea as KCT0000452). This is to determine whether the intake of JBD301 in overweight or obese subjects is effective in reducing body weight or body fat. The clinical trial design of JBD301 is shown in FIG. 12.

Participating subjects were recruited according to clinical trial protocols approved by the IRB. Study participants were enrolled for the study if they satisfied the following criteria: 1) written informed consent, 2) men or women 25-65 years of age, and 3) body mass index of 25-35 kg/m². The exclusion criteria included the following: subjects who received antibiotics within 12 weeks prior to the first visit; subjects with current use of medications for body weight reduction (lipase inhibitors, anti-depressants, appetite suppressants), diuretics, contraceptives, steroids, and hormones; subjects who were involved in commercial diet programs or were under a diet formula within 12 weeks prior to the first visit; subjects with uncontrolled hypertension or diabetes; subjects with current medical conditions including cardiac, renal, hepatic, neurovascular, thyroid or parathyroid disorders/diseases; subjects with medical conditions including depression, schizophrenia, psychosis, alcohol abuse or drug abuse; subjects diagnosed with cancer within the past 5 years; subjects with hyper-allergic reactions to components in the testing food; subjects who were planning to reduce body weight by food and exercise during the clinical trial period; and subjects that were pregnant or breast-feeding.

The subjects were instructed to maintain their usual diet with no intake of probiotics, antibiotics or agents known to affect body weight. The enrolled subjects were simply randomized for parallel assignment. The study consisted of daily administration of 1 capsule of either *Lactobacillus* JBD301 (10[9] CFU) or placebo for 12 weeks without any dietary restriction. In a capsule of 450 mg, major ingredient, either JBD301 powder or non-dairy coffee creamer, is 12% while other excipients include 40% skim milk, 40% sucrose and 8% ascorbic acid.

FIG. 13 presents the assignment of control and experimental for subjects screened in this trial for efficacy of said anti-obesity *Lactobacillus reuteri* JBD301 (KCTC 12606BP) following the method in Example 3. The total 40 subjects were enrolled and 37 subjects finished the trial. The study participant's baseline characteristics were shown in Table 2.

TABLE 2

| Variable | Group | | P value |
| --- | --- | --- | --- |
| | *L. reuteri* JBD301 | Control | |
| All participants | 18 (48.6) | 19 (51.4) | 0.103 |
| Sex, male | 7 (38.9) | 13 (68.4) | |
| Sex, female | 11 (61.1) | 6 (31.6) | |
| Age mean ± SEM | 39.4 ± 2.7 | 42.1 ± 3.1 | 0.578 |
| Height mean ± SEM | 165.0 ± 2.4 | 169.0 ± 2.3 | 0.233 |
| Weight mean ± SEM | 79.6 ± 3.4 | 80.1 ± 3.0 | 0.822 |
| BMI mean ± SEM | 29.0 ± 0.7 | 27.9 ± 0.5 | 0.150 |

The primary outcome from this study was body weight in obese adults. The adipose tissue area and body fat mass of each subject were measured using computerized tomography (CT) and Dual-Emission X-ray Absorptiometry (DEXA), respectively. For the clinical data, the statistical analysis was performed using procedures in SAS (Version 9.2) and MedCalc (Version 11.6.0). Depending on the normality of the underlying data, the Mann-Whitney U test and the Wilcoxon Signed Rank test were used to perform statistical analyses.

The Mann-Whitney U test was used to compare the outcome variables. The percentage change in outcome variables at 12 weeks (%) was calculated by the following formula: ((value at 12 weeks—value at 0 week)/value at 0 week)×100. Without any dietary restrictions or additional exercise, changes in the body weight from baseline to endpoint were 0.31% (0.21 kg) in the *Lactobacillus* JBD301 group and 1.77% (1.45 kg) in the placebo group, resulting in a 1.46% (1.24 kg) between-group difference. A Mann-Whitney U test showed that there was a statistically significant difference in the percentage change of weight between the *Lactobacillus* JBD301 and the placebo group (P=0.026) as well as in the BMI (P=0.036) from the 0 week assessment to the 12 weeks assessment.

TABLE 3

| | | | | | (Unit: %) |
| --- | --- | --- | --- | --- | --- |
| | *L. reuteri* JBD301 | | Control | | |
| % change in Variable | n | Mean ± SEM | n | Mean ± SEM | P value |
| Total abdominal Fat area (cm²) | 18 | 1.64 ± 4.26 | 19 | 3.45 ± 4.23 | 1.000 |
| Body fat mass (g) | 18 | −0.38 ± 2.09 | 19 | 3.41 ± 1.17 | 0.053 |
| Weight (kg) | 18 | 0.31 ± 0.71 | 19 | 1.77 ± 0.40 | 0.026* |
| BMI (kg/m²) | 18 | 0.32 ± 0.76 | 19 | 1.65 ± 0.46 | 0.036* |
| Hip circumstance (cm) | 18 | −0.20 ± 0.45 | 19 | 0.76 ± 0.31 | 0.126 |
| HbA1c (%) | 18 | −1.61 ± 1.02 | 19 | 1.39 ± 1.16 | 0.118 |

*P values were obtained from Mann-Whitney U test, significant difference if P value is ≤ 0.05.

The Wilcoxon Signed Rank test was used to compare the percentage differences in outcome variables for the two treatment groups. The percentage differences in outcome variables were calculated by the following formula: (value of experimental/value of placebo)×100. Wilcoxon Signed Rank test confirmed that there was a statistically significant difference in the pairwise comparison of the percentage between 97.94% of JBD301 group (n=18) and 100% of control group (n=19)(P=0.028).

TABLE 4

| | 0 week | 12 week | (Unit: %) P value |
| --- | --- | --- | --- |
| % control in body weight | 99.45 ± 4.26 | 97.94 ± 4.21 | 0.028* |

*P values were obtained from Wilcoxon signed rank test, significant difference if P value is ≤ 0.05. Values are mean ± SEM.

FIG. 14 presents the result of clinical trial for efficacy of said anti-obesity *Lactobacillus reuteri* JBD301 (KCTC 12606BP) following the method in Example 3. FIG. 14 confirms that there was a statistically significant difference in body weight of JBD301 group from the control group in clinical trial. Body weight or body fat is significantly affected by factors that often change due to external environmental factors such as food intake or exercise habits. Considering this, the difference between the control and experimental groups is very important.

INDUSTRIAL APPLICABILITY

According to the present invention, the use of an intestinal strain having the ability to inhibit obesity by reducing the concentration of fatty acid dissolved in gut fluid content in the mammalian gastrointestinal tract enables the development of an anti-obesity drug that can be generally utilized by patients already suffering from obesity, whereby a significant contribution to human health can be expected.

The invention claimed is:

1. A method for promoting weight loss in a mammal by lowering fatty acid concentration of gut fluid in a gastrointestinal tract of the mammal, said method consisting of administering an effective amount of one or more strains selected from the group consisting of *Lactobacillus reuteri* JBD301 (KCTC 12606BP), *Lactobacillus plantarum* JBD302 (KCTC 12918BP), *Lactobacillus casei* JBD303 (KCTC 12919BP), *Lactobacillus casei* JBD304 (KCTC 12920BP), *Lactobacillus paracasei* JBD305 (KCTC 12921BP), *Lactobacillus alimentarius* JBD306 (KCTC 12922BP), *Lactobacillus delbrueckii* subsp. *Lactis* JBD307 (KCTC 12923BP), *Lactobacillus pantheris* JBD308 (KCTC 12924BP), *Lactobacillus fermentum* JBD309 (KCTC 12925BP), *Lactobacillus rhamnosus* JBD311 (KCTC 12926BP), *Lactobacillus salivarius* subsp. *salicinius* JBD312 (KCTC 12927BP), *Lactobacillus mali* JBD313 (KCTC 12928BP), *Streptococcus lutetiensis* JBD314 (KCTC 12929BP), and *Lactococcus lactis* subsp. *Lactis* JBD315 (KCTC 12930BP), or a culture thereof, to the mammal.

2. The method of claim 1, wherein the one or more strains or the culture thereof are administered as a pharmaceutical composition.

3. The method of claim 1, wherein the one or more strains or the culture thereof are administered as a foodstuff.

4. The method of claim 2, wherein the pharmaceutical composition contains the one or more strains in an amount of $10^3$-$10^{12}$ cfu/g of composition.

5. The method of claim 3, wherein the foodstuff contains the one or more strains in an amount of $10^3$-$10^{12}$ cfu/g of composition.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: primer 27 F

<400> SEQUENCE: 1
agagtttgat cctggctcag                                                    20

<210> SEQ ID NO 2
<211> LENGTH: 19
<212> TYPE: DNA
<213> ORGANISM: Artificial Sequence
<220> FEATURE:
<223> OTHER INFORMATION: primer 1492R

<400> SEQUENCE: 2
ggttaccttg ttacgactt                                                     19

<210> SEQ ID NO 3
<211> LENGTH: 1472
<212> TYPE: DNA
<213> ORGANISM: Lactobacillus reuteri
<220> FEATURE:
<221> NAME/KEY: misc_feature
<222> LOCATION: 6..6
<223> OTHER INFORMATION: a or g or c or t
<220> FEATURE:
<221> NAME/KEY: misc_feature
<222> LOCATION: 8..8
<223> OTHER INFORMATION: a or g or c or t
<220> FEATURE:
<221> NAME/KEY: misc_feature
<222> LOCATION: 1466..1466
<223> OTHER INFORMATION: a or g or c or t

<400> SEQUENCE: 3
cgcggntncc tatcatgcag tcgttacgca ctggcccaac tgattgatgg tgcttgcacc          60
tgattgacga tggatcacca gtgagtggcg gacgggtgag taacacgtag gtaacctgcc         120
ccggagcggg ggataacatt tggaaacaga tgctaatacc gcataacaac aaaagccaca         180
tggcttttgt ttgaaagatg gctttggcta tcactctggg atggacctgc ggtgcattag         240
ctagttggta aggtaacggc ttaccaaggc gatgatgcat agccgagttg agagactgat         300
cggccacaat ggaactgaga cacggtccat actcctacgg gaggcagcag tagggaatct         360
tccacaatgg gcgcaagcct gatggagcaa cmccscgtra gtgaagaarg gttttcggct         420
cgtaaaagct ytgttgttgr agaagaacgt gcgtgagagt aactgttcac gcagtgacgg         480
tatccaacca gaaaagtcac ggctaactac gtgccagcag ccgcggtaat acgtaggtgg         540
caagcgttat ccggatttat tgggcgtaaa gcgagcgcag gcggttgct taggtctgat         600 gtgaaagcct tcggcttaac cgaagaagtg catcggaaac cgggcgactt gagtgcagaa         660
gaggacagtg gaactccatg tgtagcggtg gaatgcgtag atatatggaa gaacaccagt         720
ggcgaaggcg gctgtctggt ctgcaactga cgctgaggct cgaaagcatg ggtagcgaac         780
aggattagat accctggtag tccatgccgt aaacgatgag tgctaggtgt tggagggttt         840
ccgcccttca gtgccggagc taacgcatta agcactccgc ctggggagta cgaccgcaag         900
gttgaaactc aaaggaattg acgggggccc scacaagcgg tggagcatgt ggtttaattc         960
gaasctacgc gaaraacctt accaggtctt tgacatcttg cgctaacctt ararawaaag        1020

```
gcgttccctt cggggacsca atgacaggtg gtgcatggtc stcstcagct ccgtgtcgtg      1080
agatgttggg ttaagtcccg caacgagcgc aaccttgtt actagttgcc agcattaagt       1140
tgggcactct agtgagactg ccggtgacaa accggaggaa ggtggggacg acgtcagatc      1200
atcatgcccc ttatgacctg gctacacac gtgctacaat ggacggtaca acgagtcgca       1260
agctcgcgag agtaagctaa tctcttaaag ccgttctcag ttcggactgt aggctgcaac     1320
tcgcctacac gaagtcggaa tcgctagtaa tcgcggatca gcatgccgcg gtgaatacgt     1380
tcccgggcct tgtacacacc gcccgtcaca ccatgggagt ttgtaacgcc caaagtcggt     1440
ggcctaacct ttatgaggag ccgctnaggc ga                                    1472
```

<210> SEQ ID NO 4
<211> LENGTH: 1424
<212> TYPE: DNA
<213> ORGANISM: Lactobacillus plantarum

<400> SEQUENCE: 4

```
tgcagtcgac gaactctggt attgattggt gcttgcatca tgatttacat ttgagtgagt       60
ggcgaactgg tgagtaacac gtgggaaacc tgcccagaag cggggggataa cacctggaaa      120 cagatgctaa taccgcataa caacttggac cgcatggtcc gagcttgaaa gatggcttcg      180
gctatcactt ttggatggtc ccgcggcgta ttagctagat ggtggggtaa cggctcacca      240
tggcaatgat acgtagccga cctgagaggg taatcggcca cattgggact gagacacggc      300
ccaaactcct acgggaggca gcagtaggga atcttccaca atggacgaaa gtctgatgga      360
gcaacgccgc gtgagtgaag aagggttcg gctcgtaaaa ctctgttgtt aaagaagaac       420
atatctgaga gtaactgttc aggtattgac ggtatttaac cagaaagcca cggctaacta     480
cgtgccagca gccgcggtaa tacgtaggtg gcaagcgttg tccggattta ttgggcgtaa     540
agcgagcgca ggcggttttt taagtctgat gtgaaagcct tcggctcaac cgaagaagtg    600
catcggaaac tgggaaactt gagtgcagaa gaggacagtg gaactccatg tgtagcggtg    660
aaatgcgtag atatatggaa gaacaccagt ggcgaaggcg gctgtctggt ctgtaactga    720
cgctgaggct cgaaagtatg ggtagcaaac aggattagat accctggtag tccataccgt   780
aaacgatgaa tgctaagtgt tggagggttt ccgcccttca gtgctgcagc taacgcatta    840
agcattccgc ctggggagta cggccgcaag gctgaaactc aaaggaattg acgggggccc    900
gcacaagcgg tggagcatgt ggtttaattc gaagctacgc gaagaacctt accaggtctt    960
gacatactat gcaaatctaa gagattagac gttcccttcg gggacatgga tacaggtggt   1020
gcatggttgt cgtcagctcg tgtcgtgaga tgttgggtta agtcccgcaa cgagcgcaac   1080
ccttattatc agttgccagc attaagttgg gcactctggt gagactgccg gtgacaaacc   1140
ggaggaaggt ggggatgacg tcaaatcatc atgcccctta tgacctgggc tacacacgtg   1200
ctacaatgga tggtacaacg agttgcgaac tcgcgagagt aagctaatct cttaaagcca   1260
ttctcagttc ggattgtagg ctgcaactcg cctacatgaa gtcggaatcg ctagtaatcg   1320
cggatcagca tgccgcggtg aatacgttcc cgggccttgt acacaccgcc cgtcacacca    1380
tgagagtttg taacacccaa agtcggtggg gaacctttag aacc                      1424
```

<210> SEQ ID NO 5
<211> LENGTH: 1422
<212> TYPE: DNA
<213> ORGANISM: Lactobacillus casei

<400> SEQUENCE: 5

```
gacgagttct cgttgatgat cggtgcttgc accgagatta acatggaacg agtggcggac      60
gggtgagtaa cacgtgggta acctgcccct taagtggggga taacatttgg aaacagatgc    120
taataccgca tagatccaag aaccgcatgg ttcttggctg aaagatgcg taagctatcg      180
cttttggatg gacccgcggc gtattagcta gttggtgagg taatggctca ccaaggccga    240
tgatacgtag ccgaactgag aggttgatcg gccacattg ggactgagac acggccccaa     300
actcctacgg gaggcagcag tagggaatct ttccacaatg gacgcaagtc tgatggagca    360
acgccgcgtg agtgaagaag ctttcgggt cgtaaaactc tgttgttgga gaagaatggt    420
cggcagagta actgttgtcg gcgtgacggt atccaaccag aaagccacgg ctaactacgt    480
gccagcagcc gcggtaatac gtaggtggca agcgttatcc ggatttattg ggcgtaaagc    540
gagcgcaggc ggttttttaa gtctgatgtg aaagccctcg gcttaaccga ggaagcgcat    600
cggaaactgg gaaacttgag tgcagaagag gacagtggaa ctccatgtgt agcggtgaaa    660
tgcgtagata tatggaagaa caccagtggc gaaggcggct gtctggtctg taactgacgc    720
tgaggctcga aagcatgggt agcgaacagg attagatacc ctggtagtcc atgccgtaaa    780
cgatgaatgc taggtgttgg aggtttccg cccttcagtg ccgcagctaa cgcattaagc     840
attccgcctg ggagtacga ccgcaaggtt gaaactcaaa ggaattgacg ggggcccgca    900
caagcggtgg gagcatgtgg tttaattcga agcaacgcga gaaaccttta ccaggtcttg    960
acatctttt gatcacctga aagatcaggt ttccccttc gggggcaaaa tgacaggtgg     1020
tgcatggttg tcgtcagctc gtgtcgtgag atgttgggtt aagtcccgca acgagcgcaa    1080
cccttatgac tagttgccag catttagttg ggcactctag taagactgcc ggtgacaaac    1140
cggaggaagg tggggatgac gtcaaatcat catgcccctt atgacctggg ctacacacgt    1200
gctacaatgg atggtacaac gagttgcgag accgcgaggt caagctaatc tcttaaagcc    1260
attctcagtt cggactgtag gctgcaactc gcctacacga agtcggaatc gctagtaatc    1320
gcggatcagc acgccgcggt gaatacgttc ccgggccttg tacacaccgc ccgtcacacc    1380
atgagagttg taacacccga agccggtggc gaacccttta gg                       1422
```

<210> SEQ ID NO 6
<211> LENGTH: 1418
<212> TYPE: DNA
<213> ORGANISM: Lactobacillus casei

<400> SEQUENCE: 6

```
gacgagttct cgttgatgat cggtgcttgc accgagattc aacatggaac gagtggcgga     60
cgggtgagta acacgtgggt aacctgccct taagtggggg ataacatttg aaacagatg     120
ctaataccgc atagatccaa gaaccgcatg gttcttggct gaaagatggc gtaagctatc    180
gcttttggat ggacccgcgg cgtattagct agttggtgag gtaatggctc accaaggcga    240
tgatacgtag ccgaactgag aggttgatcg gccacattgg gactgagaca cggcccaaac    300
tcctacggga ggcagcagta gggaatcttc acaatggacg caagtctga tggagcaacg     360
cccgcgtgag tgaagaaggc tttcgggtcg taaaactctg ttgttggaga agaatggtcg    420
gcagagtaac tgttgtcggc gtgacggtat ccaaccagaa agccacggct aactacgtgc    480
cagcagccgc ggtaatacgt aggtggcaag cgttatccgg atttattggg cgtaaagcga    540
gcgcaggcgg ttttttaagt ctgatgtgaa agccctcggc ttaaccgagg aagcgcatcg    600
gaaactggga aacttgagtg cagaagagga cagtggaact ccatgtgtag cggtgaaatg    660
```

```
cgtagatata tggaagaaca ccagtggcga aggcggctgt ctggtctgta actgacgctg    720
aggctcgaaa gcatgggtag cgaacaggat tagatacccT ggtagtccat gccgtaaacg    780
atgaatgcta ggtgttggag ggtttccgcc cttcagtgcc gcagctaacg cattaagcat    840
tccgcctggg gagtacgacc gcaaggttga aactcaaagg aattgacggg gcccgcaca     900 agcggtggag catgtggttt aattcgaagc aacgcgaaga accttaccag gtcttgacat    960
cttttgatca cctgagagat caggtttccc cttcgggggc aaaatgacag gtggtgcatg   1020
gttgtcgtca gctcgtgtcg tgagatgttg ggttaagtcc cgcaacgagc gcaacccttA   1080
tgactagttg ccagcattta gttgggcact ctagtaagac tgccggtgac aaaccggagg   1140
aaggtgggga tgacgtcaaa tcatcatgcc ccttatgacc tgggctacac acgtgctaca   1200
atggatggta caacgagttg cgagaccgcg aggtcaagct aatctcttaa agccattctc   1260
agttcggact gtaggctgca actcgcctac acgaagtcgg aatcgctagt aatcgcggat   1320
cagcacgccg cggtgaatac gttcccgggc cttgtacaca ccgcccgtca caccatgaga   1380
gtttgaacac ccgaagccgg tggcgaaccc tttaggag                           1418
```

<210> SEQ ID NO 7
<211> LENGTH: 1420
<212> TYPE: DNA
<213> ORGANISM: Lactobacillus paracasei

<400> SEQUENCE: 7

```
atgatcggtg cttgcaccga gattcaacat ggaacgagtg gcggacgggt gagtaacacg     60
tgggtaacct gcccttaagt gggggataac atttggaaac agatgctaat accgcataga    120
tccaagaacc gcatggttct ggctgaaag atggcgtaag ctatcgcttt tggatggacc     180
cgcggcgtat tagctagttg gtgaggtaat ggctcaccaa ggcgatgata cgtagccgaa    240
ctgagaggtt gatcggccac attgggactg agacacggcc caaactccta cgggaggcag    300
cagtagggaa tcttccacaa tggacgcaag tctgatggag caacgccgcg tgagtgaaga    360
aaggcttttc gggttcgtaa aacttctgtt gttggagaag aaatggtcgg cagagtaact    420
gttgttcggc gtgacggtat ccaaccagaa aagccacggc taactacgtg ccagcagccg    480
cggtaatacg taggtggcaa gcgttatccg gatttattgg gcgtaaagcg agcgcaggcg    540
gttttttaag tctgatgtga aagccctcgg cttaaccgag gaagcgcatc ggaaactggg    600
aaacttgagt gcagaagagg acagtggaac tccatgtgta gcggtgaaat gcgtagatat    660
atggaagaac accagtggcg aaggcggctg tctggtctgt aactgacgct gaggctcgaa    720
agcatgggta gcgaacagga ttagataccc tggtagtcca tgccgtaaac gatgaatgct    780
aggtgttgga gggtttccgc ccttcagtgc cgcagctaac gcattaagca ttccgcctgg    840
ggagtacgac cgcaaggttg aaactcaaag gaattgacgg gggcccgcac aagcggtggg    900
agcatgtggt tttaattcga agcaacgcga aaaacttta ccagggtctt gaacatcttt    960
ttgatcacct gaaaagatca ggtttccccc ttcgggggc aaaatgacag ggggtgcat    1020 gggttgtcgt cagctcgtgt cgtgagatgt tgggttaagt cccgcaacga gcgcaaccct   1080
tatgactagt tgccagcatt tagttgggca ctctagtaag actgccggtg acaaaccgga   1140
ggaaggtggg gatgacgtca atcatcatg cccttatga cctgggctac acacgtgcta    1200
caatggatgg tacaacgagt tgcgagaccg cgaggtcaag ctaatctctt aaagccattc   1260
tcagttcgga ctgtaggctg caactcgcct acacgaagtc ggaatcgcta gtaatcgcgg   1320
```

```
atcagcacgc cgcggtgaat acgttcccgg gccttgtaca caccgcccgt cacaccatga    1380
gagtttgtaa cacccgaagc cggtggcgaa ccctttagga                          1420

<210> SEQ ID NO 8
<211> LENGTH: 1430
<212> TYPE: DNA
<213> ORGANISM: Lactobacillus alimentarius

<400> SEQUENCE: 8
cagtcgacga gttctgatta ttgaaaggtg cttgcatctt gatttaattt tgaacgagtg     60
gcggacgggt gagtaacacg tgggtaacct gcccttaagt gggggataac atttggaaac    120
agatgctaat accgcataaa tccaagaacc gcatggttct tggctgaaag atggcgtaag    180
ctatcgcttt tggatggacc cgcggcgtat tagctagttg gtgaggtaac ggctcaccca    240
aggcaatgat acgtagccga actgagaggt tgatcggcca ccattgggac tgagacacgg    300
ccccaaactc ctacgggagg cagcagtagg gaatctttcc acaatggacg caagtctgat    360
ggagcaacgc cgcgtgagtg aagaaggctt cgggtcgta aaactctgtt gttggagaag    420
aatggtcggc agagtaactg ttgtcggcgt gacggtatcc aaccagaaag ccacggctaa    480
ctacgtgcca gcagccgcgg taatacgtag gtggcaagcg ttatccggat ttattgggcg    540
taaagcgagc gcaggcggtt ttttaagtct gatgtgaaag ccctcggctt aaccgaggaa    600
gtgcatcgga aactgggaaa cttgagtgca gaagaggaca gtggaactcc atgtgtagcg    660
gtgaaatgcg tagatatatg gaagaacacc agtggcgaag cggctgtct ggtctgtaac    720 tgacgctgag gctcgaaagc atgggtagcg aacaggatta gataccctgg tagtccatgc    780
cgtaaacgat gaatgctagg tgttggaggg tttccgccct tcagtgccgc agctaacgca    840
ttaagcattc cgcctgggga gtacgaccgc aaggttgaaa ctcaaaggaa ttgacggggg    900
cccgcacaag cggtggagca tgtggtttaa ttcgaagcaa cgcgaagaac cttaccaggt    960
cttgacatct tttgatcacc tgaagagatc aggtttcccc cttcggggc aaaatgacag   1020 gtggtgcatg gttgtcgtca gctcgtgtcg tgagatgttg ggttaagtcc cgcaacgagc   1080 gcaacccttta tgactagttg ccagcatttta gttgggcact ctagtaagac tgccggtgac   1140
aaaccgaagg aaggtgggga tgacgtcaaa tcatcatgcc ccttatgacc tgggctacac   1200
acgtgctaca atggatggta caacgagttg cgagaccgcg aggtcaagct aatctcttaa   1260
agccattctc agttcggact gtaggctgca actcgcctac acgaagtcgg aatcgctagt   1320
aatcgcggat cagcacgccg cggtgaatac gttcccgggc cttgtacaca ccgcccgtca   1380
caccatgaga gtttgtaaca cccgaagccg gtggcgaacc ctttaggagc              1430

<210> SEQ ID NO 9
<211> LENGTH: 1414
<212> TYPE: DNA
<213> ORGANISM: Lactobacillus delbrueckii

<400> SEQUENCE: 9
gacgagttct cgttgatgat cggtgcttgc accgagattc aacatggaac gagtggcgga     60
cgggtgagta acacgtgggt aacctgccct taagtggggg ataacatttg aaacagatg    120 ctaataccgc atagatccaa gaaccgcatg gttcttggct gaaagatggc gtaagctatc    180
gcttttggat ggacccgcgg cgtattagct agttggtgag gtaatggctc accaaggcga    240
tgatacgtag ccgaactgag aggttgatcg gcccacattg gactgagac acggccccaa    300 actcctacgg gaggcagcag tagggaatct tccaccaatg gacgcaagtc tgatggagca    360
```

```
acgccgcgtg agtgaagaag gctttcgggt cgtaaaactc tgttgttgga gaagaatggt      420
cggcagagta actgttgtcg gcgtgacggt atccaaccag aaagccacgg ctaactacgt      480
gccagcagcc gcggtaatac gtaggtggca agcgttatcc ggatttattg ggcgtaaagc      540
gagcgcaggc ggtttttttaa gtctgatgtg aaagccctcg gcttaaccga ggaagcgcat      600
cggaaactgg gaaacttgag tgcagaagag gacagtggaa ctccatgtgt agcggtgaaa      660
tgcgtagata tatggaagaa caccagtggc gaaggcggct gtctggtctg taactgacgc      720
tgaggctcga aagcatgggt agcgaacagg attagatacc ctggtagtcc atgccgtaaa      780
cgatgaatgc taggtgttgg agggtttccg cccttcagtg ccgcagctaa cgcattaagc      840
attccgcctg gggagtacga ccgcaaggtt gaaactcaaa ggaattgacg ggggcccgca      900
caagcggtgg agcatgtggt ttaattcgaa gcaacgcgaa gaaccttacc aggtcttgac      960
atcttttgat cacctgagag atcaggtttc cccttcgggg gcaaaatgac aggtggtgca     1020
tggttgtcgt cagctcgtgt cgtgagatgt tgggttaagt cccgcaacga gcgcaaccct     1080
tatgactagt tgccagcatt tagttgggca ctctagtaag actgccggtg acaaaccgga     1140
ggaaggtggg gatgacgtca atcatcatg ccccttatga cctgggctac acacgtgcta     1200
caatggatgg tacaacgagt tgcgagaccg cgaggtcaag ctaatctctt aaagccattc     1260
tcagttcgga ctgtaggctg caactcgcct acacgaagtc ggaatcgcta gtaatcgcgg     1320
atcagcacgc cgcggtgaat acgttcccgg gccttgtaca ccgcccgt cacaccatga     1380
gagtttgtaa cacccgaagc cggtggcgaa ccct     1414
```

<210> SEQ ID NO 10
<211> LENGTH: 1435
<212> TYPE: DNA
<213> ORGANISM: Unknown
<220> FEATURE:
<223> OTHER INFORMATION: Lactobacillus pantheris

<400> SEQUENCE: 10

```
gcagtcgagc gacttactaa atgaatgcgg tgcttgcacc aagtgatttt agagcggtga       60
gcggcggatg ggtgagtaac acgtgggtaa cctgcctcta agcaggggat aacatttgga      120
aacagatgct aataccgtat aaatcctaaa accacatggt tttaggctga aaggcggctt      180
cggctgtcac ttagagatgg acccgcggcg tattagctag ttggtgaggt aatggctcac      240
caaggcaatg atacgtagcc gaactgagag gttgatcggc cacattggga ctgagacacg      300
gcccaaactc ctacgggagg cagcagtagg gaatcttcca caatgacgc aagtctgatg      360
gagcaacgcc gcgtgagtga agaaggcttt cgggtcgtaa aactctgttg ttgaagaaga      420
acacgtttga gagtaactgt tcagacgttg acggtattca accagaaagc cacggctaac      480
tacgtgccag cagccgcggt aatacgtagg tggcaagcgt tatccggatt tattgggcgt      540
aaagcgagcg caggcggttt tttaagtctg atgtgaaagc cctcggctta accgaggaag      600
tgcatcggaa actgggaaac ttgaatgctg aagaggacag tggaactcca tgtgtagcgg      660
tgaaatgcgt agatatatgg aagaacacca gtggcgaagg cggctgtctg gtcagttatt      720
gacgctgagg ctcgaaagca tgggtagcga acaggattag ataccctggt agtccatgcc      780
gtaaacgatg aatactaggt gttggagggt ttccgccctt cagtgccgca gctaacgcat      840
taagtattcc gcctggggag tacgaccgca aggttgaaac tcaaaggaat tgacgggggc      900
ccgcacaagc ggtggagcat gtggtttaat tcgaagcaac gcgaagaacc ttaccaggtc      960
```

```
ttgacatctt ctgctatttc tagagataga aagttcccct tcggggacgg aatgacaggt      1020
gggtgcatgg gttgtcgtca gcctcgtgtc gtgaagatgt tgggttaagt cccgcaacga      1080
gcgcaaccct tatgactagt tgccagcatt aagttgggca ctctagtaag actgccggtg      1140
acaaaccgga ggaaggtggg gacgacgtca aatcatcatg ccccttatga cctgggctac      1200
acacgtgcta caatggttgg tacaacgagt tgcgaactcg cgagggtaag ctaatctctt      1260
aaagccaatc tcagttcgga ctgtaggctg caactcgcct acacgaagtc ggaatcgcta      1320
gtaatcgcgg atcagcatgc cgcggtgaat acgttcccgg gccttgtaca caccgcccgt      1380
cacaccatga gagtttgtaa cacccaaagc cggtggggca ccctcgggag cagcc           1435
```

```
<210> SEQ ID NO 11
<211> LENGTH: 1432
<212> TYPE: DNA
<213> ORGANISM: Lactobacillus fermentum

<400> SEQUENCE: 11
tcgacgcgtt ggcccattga ttgacggtgc ttgcacctga ttgattttgg tcgccaacga        60
gtggcggacg ggtgagtaac acgtaggtaa cctgcccaga agcgggggac aacatttgga      120
aacagatgct aataccgcat aacagcgttg ttcgcatgaa caacgcttaa aagatggctt      180
ctcgctatca cttctggatg gacctgcggt gcattagctt gttggtgggg taacggccta      240
ccaaggcgat gatgcatagc cgagttgaga gactgatcgg ccacaatggg actgagacac      300
ggcccatact cctacgggag gcagcagtag ggaatcttte cacaatgggg cgcaagccct      360
gatggagcca acaccggcgt gagtgaagaa agggtttcgg ctcgtaaagc tctgttgtta      420
aagaagaaca cgtatgagag taactgttca tacgttgacg gtatttaacc agaaagtcac      480
ggctaactac gtgccagcag ccgcggtaat acgtaggtgg caagcgttat ccggatttat      540
tgggcgtaaa gagagtgcag gcggttttct aagtctgatg tgaaagcctt cggcttaacc      600
ggagaagtgc atcggaaact ggataacttg agtgcagaag agggtagtgg aactccatgt      660
gtagcggtgg aatgcgtaga tatatggaag aacaccagtg gcgaaggcgg ctacctggtc      720
tgcaactgac gctgagactc gaaagcatgg gtagcgaaca ggattagata ccctggtagt      780
ccatgccgta aacgatgagt gctaggtgtt ggagggtttc cgcccttcag tgccggagct      840
aacgcattaa gcactccgcc tggggagtac gaccgcaagg ttgaaactca aaggaattga      900
cgggggcccg cacaagcggt ggagcatgtg gtttaattcg aagctacgcg aagaaccttta     960 ccaggtcttg acatcttgcg ccaacccctag agatagggcg ttttccttcg ggaacgcaat     1020
gacagggtgg tgcatggtcg tcgtcagctc gtgtcgtgag atgttgggtt aagtcccgca     1080
acgagcgcaa cccttgttac tagttgccag cattaagttg ggcactctag tgagactgcc     1140
ggtgacaaac cggaggaagg tggggacgac gtcagatcat catgccccctt atgacctggg     1200 ctacacacgt gctacaatgg acggtacaac gagtcgcgaa ctcgcgaggg caagcaaatc     1260
tcttaaaacc gttctcagtt cggactgcag gctgcaactc gcctgcacga agtcggaatc     1320
gctagtaatc gcggatcagc atgccgcggt gaatacgttc ccgggccttg tacacaccgc     1380
ccgtcacacc atgagagttt gaacacccaa agtcggtggg gaacctttag ag             1432
```

```
<210> SEQ ID NO 12
<211> LENGTH: 1421
<212> TYPE: DNA
<213> ORGANISM: Lactobacillus rhamnosus

<400> SEQUENCE: 12
```

```
gacgagttct gattattgaa aggtgcttgc atcttgattt aattttgaac gagtggcgga    60
cgggtgagta acacgtgggt aacctgccct taagtggggg ataacatttg gaaacagatg   120
ctaataccgc ataaatccaa gaaccgcatg gttcttggct gaaagatggc gtaagctatc   180
gcttttggat ggacccgcgg cgtattagct agttggtgag gtaacggctc accaaggcaa   240
tgatacgtag ccgaactgag aggttgatcg gccacattgg gactgagaca cgggcccaaa   300
ctccttacgg gaggcagcag tagggaatct tccacaatgg acgcaagtc tgatggagca   360
acgccgcgtg agtgaagaag gctttcgggt cgtaaaactc tgttgttgga agaatggt    420
cggcagagta actgttgtcg gcgtgacggt atccaaccag aaagccacgg ctaactacgt   480
gccagcagcc gcggtaatac gtaggtggca agcgttatcc ggatttattg ggcgtaaagc   540
gagcgcaggc ggttttttaa gtctgatgtg aaagccctcg gcttaaccga ggaagtgcat   600
cggaaactgg aaaacttgag tgcagaagag gacagtggaa ctccatgtgt agcggtgaaa   660
tgcgtagata tatggaagaa caccagtggc gaaggcggct gtctggtctg taactgacgc   720
tgaggctcga aagcatgggt agcgaacagg attagatacc ctggtagtcc atgccgtaaa   780
cgatgaatgc taggtgttgg agggtttccg cccttcagtg ccgcagctaa cgcattaagc   840
attccgcctg gggagtacga ccgcaaggtt gaaactcaaa ggaattgacg ggggcccgca   900
caagcggtgg agcatgtggt ttaattcgaa gcaacgcgaa gaaccttacc aggtcttgac   960
atcttttgat cacctgagag atcaggtttc cccttcgggg gcaaaatgac aggtggtgca  1020
tggttgtcgt cagctcgtgt cgtgagatgt tgggttaagt cccgcaacga gcgcaaccct  1080
tatgactagt tgccagcatt tagttgggca ctctagtaag actgccggtg acaaaccgga  1140
ggaaggtggg gatgacgtca aatcatcatg ccccttatga cctgggctac acacgtgcta  1200
caatggatgg tacaacgagt tgcgagaccg cgaggtcaag ctaatctctt aaagccattc  1260
tcagttcgga ctgtaggctg caactcgcct acacgaagtc ggaatcgcta gtaatcgcgg  1320
atcagcacgc cgcggtgaat acgttcccgg gccttgtaca caccgcccgt cacaccatga  1380
gagtttgtaa cacccgaagc cggtggcgaa ccctttagga g                      1421
```

<210> SEQ ID NO 13
<211> LENGTH: 1417
<212> TYPE: DNA
<213> ORGANISM: Lactobacillus salivarius

<400> SEQUENCE: 13

```
gcagtcgacg aactttctta caccgaatgc ttgcattcat cgtaagaagt tgagtggcgg    60
acgggtgagt aacacgtggg taacctgcct aaaagaaggg gataacactt ggaaacaggt   120
gctaataccg tatatctcta aggatcgcat gatccttaga tgaaagatgg ttctgctatc   180
gcttttagat ggacccgcgg cgtattaact agttggtggg gtaacggcct accaaggtga   240
tgatacgtag ccgaactgag aggttgatcg gccacattgg gactgagaca cggcccaaac   300
tcctacggga ggcagcagta gggaatcttc cacaatggac gcaagtctga tggagcaacg   360
ccggcgtgag tgaagaaggt ctttcggatc gtaaaactct gttgttagag aagaacacga   420
gtgagagtaa ctgttcattc gatgacggta tctaaccagc aagtcacggc taactacgtg   480
ccagcagccg cggtaatacg taggtggcaa gcgttgtccg gatttattgg gcgtaaaggg   540
aacgcaggcg gtcttttaag tctgatgtga aagccttcgg cttaaccgga gtagtgcatt   600
ggaaactgga agacttgagt gcagaagagg agagtggaac tccatgtgta gcggtgaaat   660
```

```
gcgtagatat atggaagaac accagtggcg aaagcggctc tctggtctgt aactgacgct      720
gaggttcgaa agcgtgggta gcaaacagga ttagataccc tggtagtcca cgccgtaaac      780
gatgaatgct aggtgttgga gggtttccgc ccttcagtgc cgcagctaac gcaataagca      840
ttccgcctgg ggagtacgac cgcaaggttg aaactcaaag gaattgacgg gggcccgcac      900
aagcggtgga gcatgtggtt taattcgaag caacgcgaag aaccttacca ggtcttgaca      960
tccttttgacc acctaagaga ttaggctttc ccttcgggga caaagtgaca ggtggtgcat     1020
ggctgtcgtc agctcgtgtc gtgagatgtt gggttaagtc ccgcaacgag cgcaaccctt     1080
gttgtcagtt gccagcatta agttgggcac tctggcgaga ctgccggtga caaaccggag     1140
gaaggtgggg acgacgtcaa gtcatcatgc cccttatgac ctgggctaca cacgtgctac     1200
aatggacggt acaacgagtc gcgagaccgc gaggtttagc taatctctta aagccgttct     1260
cagttcggat tgtaggctgc aactcgccta catgaagtcg gaatcgctag taatcgcgaa     1320
tcagcatgtc gcggtgaata cgttcccggg ccttgtacac accgcccgtc acaccatgag     1380
agtttgaaca cccaaagccg gtggggaacc gcaagag                               1417

<210> SEQ ID NO 14
<211> LENGTH: 1414
<212> TYPE: DNA
<213> ORGANISM: Lactobacillus mali

<400> SEQUENCE: 14
cagtcgacgc aaactttcat cgaatgcttg cattcaccga aagttttgag tggcgaacgg      60
gtgagtaaca cgtgggtaac ctgcccagaa gaggggggata cacttggaa acaggtgcta     120
ataccgcata caataaaaaa ccgcatggtt tttatttaaa agatggttttt gctatcactt     180
ctggatggac ccgcggcgta ttagctagtt ggtaaggtaa aggcttacca aggcaatgat     240
acgtagccga actgagaggt tgatcggcca cattgggact gagacacggc ccaaactcct     300
acgggaggca gcagtaggga atcttccaca atggacgaaa gtctgatgga gcaacgccgc     360
gtgagtgaag aaggtttttcg gatcgtaaaa ctctgttgtt agagaagaac gtgtgtgaga     420
gtaactgctc atgcagtgac ggtatctaac cagaaagcca cggctaacta cgtgccagca     480
gccgcggtaa tacgtaggtg gcaagcgttg tccggattta ttgggcgtaa agggaacgca     540
ggcggttttt taagtctgat gtgaaagcct tcggcttaac cgaagtcatg cattggaaac     600
tgaaagactt gagtgcagaa gaggagagtg gaactccatg tgtagcggtg aaatgcgtag     660
atatatggaa gaacaccagt ggcgaaagcg gctctctggt ctgtaactga cgctgaggtt     720
cgaaagtgtg ggtagcaaac aggattagat accctggtag tccacaccgt aaacgatgaa     780
tgctaagtgt tggagggttt ccgcccttcg gtgctcagc taacgcatta agcattccgc      840
ctggggagta cgaccgcaag gttgaaactc aaaggaattg acggggccc gcacaagcgg     900
tggagcatgt ggtttaattc gaagcaacgc gaagaaccctt accaggtctt gacatcttct      960
gacaacctaa gaagattagg tgttcccttc ggggacagaa tgacaggtgg tgcatggttg    1020
tcgtcagctc gtgtcgtgag atgttgggt taagtcccgc aacgagcgca acccttatta     1080
ttagttgcca gcattaagtt gggcactcta gtgagactgc cggtgacaaa ccggaggaag     1140
gtggggatga cgtcaaatca tcatgcccct tatgacctgg gctacacacg tgctacaatg     1200
gacggtacaa cgagtcgcga aaccgcgagg tttagctaat ctcttaaagc cgttctcagt     1260
tcggattgta ggctgcaact cgcctacatg aagtcggaat cgctagtaat cgcggatcag     1320
catgccgcgg tgaatacgtt cccgggcctt gtacacaccg cccgtcacac catgagagtt     1380
```

| tgaacaccca aagccggtga ggaaccttat ggac | 1414 |

```
<210> SEQ ID NO 15
<211> LENGTH: 1414
<212> TYPE: DNA
<213> ORGANISM: Unknown
<220> FEATURE:
<223> OTHER INFORMATION: Lactobacillus pantheris
```

<400> SEQUENCE: 15

| gacgctgaag actttagctt gctaaagttg aagagttgc gaacgggtga gtaacgcgta | 60 |
| ggtaacctgc ctactagcgg gggataacta ttggaaacga tagctaatac cgcataacag | 120 |
| catttaaccc atgttagatg cttgaaagga gcaattgctt cactagtaga tggacctgcg | 180 |
| ttgtattagc tagttggtga ggtaacggct caccaaggcg acgatacata gccgacctga | 240 |
| gagggtgatc gggcacacac tgggacttga gaccacggcc cagacttcct acgggaggcc | 300 |
| agcagtaggg aatcttttcgg caatgggggg caaccctgac ccgagcaacg cccgcgtgag | 360 |
| tgaagaaagg ttttcggatc gtaaagctct gttgtaagag aagaaacgtg tgtgagagtg | 420 |
| gaaagttcac acagtgacgg taacttacca gaaagggacg gctaactacg tgccagcagc | 480 |
| cgcggtaata cgtaggtccc cgagcgttgt ccggatttat tgggcgtaaa gcgagcgcag | 540 |
| gcggtttaat aagtctgaag ttaaaggcag tggcttaacc attgttcgct ttggaaactg | 600 |
| ttagacttga gtgcagaagg ggagagtgga attccatgtg tagcggtgaa atgcgtagat | 660 |
| atatggagga acaccggtgg cgaaagcggc tctctggtct gtaactgacg ctgaggctcg | 720 |
| aaagcgtggg gagcaaacag gattagatac cctggtagtc cacgccgtaa acgatgagtg | 780 |
| ctaggtgtta ggccctttcc ggggcttagt gccgcagcta acgcattaag cactccgcct | 840 |
| ggggagtacg accgcaaggt tgaaactcaa aggaattgac gggggcccgc acaagcggtg | 900 |
| gagcatgtgg tttaattcga agcaacgcga agaaccttac caggtcttga catcccgatg | 960 |
| ctattcctag agataggaag tttcttcgga acatcggtga caggtggtgc atggttgtcg | 1020 |
| tcagctcgtg tcgtgagatg ttgggttaag tcccgcaacg agcgcaaccc ctattgttag | 1080 |
| ttgccatcat taagttgggc actctagcga gactgccggt aataaaccgg aggaaggtgg | 1140 |
| ggatgacgtc aaatcatcat gccccttatg acctgggcta cacacgtgct acaatggttg | 1200 |
| gtacaacgag tcgcgagtcg gtgacggcaa gcaaatctct aaagccaat ctcagttcgg | 1260 |
| attgtaggct gcaactcgcc tacatgaagt cggaatcgct agtaatcgcg gatcagcacg | 1320 |
| ccgcggtgaa tacgttcccg ggccttgaca caccgcccgt cacaccacga gagttttgtaa | 1380 |
| cacccgaagt cggtgaagaa cctttagagc cgcc | 1414 |

```
<210> SEQ ID NO 16
<211> LENGTH: 1404
<212> TYPE: DNA
<213> ORGANISM: Lactococcus lactis
<220> FEATURE:
<221> NAME/KEY: misc_feature
<222> LOCATION: 952...952
<223> OTHER INFORMATION: a or g or c or t
```

<400> SEQUENCE: 16

| gagcgctgag gttggtactt gtaccaactg gatgagcagc gaacgggtga gtaacgcgtg | 60 |
| gggaatctgc ctttgagcgg gggacaacat ttggaaacga atgctaatac cgcataaaaa | 120 |
| cttaaacac aagttttaag tttgaaagat gcaattgcat cactcaaaga tgatcccgcg | 180 |

```
ttgtattagc tagttggtga ggtaaaggct caccaaggcg atgatacata gccgacctga      240
gagggtgatc ggccacattg ggactgagac acggcccaaa ctcctacggg aggcagcagt      300
agggaatctt cggcaatgga cgaaagtctg accgagcaac gccgcgtgag tgaagaaggt      360
tttcggatcg taaaactctg ttggtagaga agaacgttgg tgagagtgga aagctcatca      420
agtgacggta actacccaga aagggacggc taactacgtg ccagcagccg cggtaatacg      480
taggtcccga gcgttgtccg gatttattgg gcgtaaagcg agcgcaggtg gtttattaag      540
tctggtgtaa aaggcagtgg ctcaaccatt gtatgcattg gaaactggta gacttgagtg      600
caggagagga gagtggaatt ccatgtgtag cggtgaaatg cgtagatata tggaggaaca      660
ccggtggcga aagcggctct ctggcctgta actgacactg aggctcgaaa gcgtggggag      720
caaacaggat tagataccct ggtagtccac gccgtaaacg atgagtgcta gatgtaggga      780
gctataagtt ctctgtatcg cagctaacgc aataagcact ccgcctgggg agtacgaccg      840
caaggttgaa actcaaagga attgacgggg gcccgcacaa gcggtggagc atgtggttta      900
attcgaagca acgcgaagaa ccttaccagg tcttgacata ctcgtgctat tnctagagat      960
aggaagttcc ttcgggacac gggatacagg tggtgcatgg ttgtcgtcag ctcgtgtcgt     1020
gagatgttgg gttaagtccc gcaacgagcg caacccctat tgttagttgc catcattaag     1080
ttgggcactc taacgagact gccggtgata aaccggagga aggtggggat gacgtcaaat     1140
catcatgccc cttatgacct gggctacaca cgtgctacaa tggatggtac aacgagtcgc     1200
gagacagtga tgtttagcta atctcttaaa accattctca gttcggattg taggctgcaa     1260
ctcgcctaca tgaagtcgga atcgctagta atcgcggatc agcacgccgc ggtgaatacg     1320
ttcccgggcc ttgtacacac cgcccgtcac accacggag ttgggagtac ccgaagtagg     1380
ttgcctaacc gcaggaggcg ttct                                             1404
```